US008765129B2

(12) United States Patent
Leung et al.

(10) Patent No.: US 8,765,129 B2
(45) Date of Patent: *Jul. 1, 2014

(54) ANTI-HEPCIDIN ANTIBODIES AND USES THEREOF

(71) Applicant: Eli Lilly and Company, Indianapolis, IN (US)

(72) Inventors: Donmienne Doen Mun Leung, San Diego, CA (US); Peng Luan, Livermore, CA (US); Barbara Anne Swanson, Encinitas, CA (US); Ying Tang, San Diego, CA (US); Derrick Ryan Witcher, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/708,059

(22) Filed: Dec. 7, 2012

(65) Prior Publication Data

US 2013/0164304 A1 Jun. 27, 2013

Related U.S. Application Data

(63) Continuation of application No. 12/872,172, filed on Aug. 31, 2010, now Pat. No. 8,329,174, which is a continuation of application No. 12/260,125, filed on Oct. 29, 2008, now Pat. No. 7,820,163.

(60) Provisional application No. 60/984,910, filed on Nov. 2, 2007.

(51) Int. Cl.
*A61K 39/395* (2006.01)

(52) U.S. Cl.
USPC ....................................................... 424/133.1

(58) Field of Classification Search
None
See application file for complete search history.

(56) References Cited

U.S. PATENT DOCUMENTS

| 7,320,894 B2 | 1/2008 | Kulaksiz et al. |
| 2004/0096987 A1 | 5/2004 | Geacintov et al. |
| 2005/0037971 A1 | 2/2005 | Nicolas et al. |
| 2006/0019339 A1 | 1/2006 | Lauth et al. |
| 2007/0224186 A1 | 9/2007 | Kulaksiz et al. |
| 2009/0136495 A1 | 5/2009 | Gately et al. |
| 2011/0027261 A1 | 2/2011 | Leung et al. |

FOREIGN PATENT DOCUMENTS

| CN | 1173737 C | 11/2004 |
| WO | 00/73454 A1 | 12/2000 |
| WO | 01/16317 A2 | 3/2001 |
| WO | 2004/058044 A2 | 7/2004 |
| WO | 2005/033327 A2 | 4/2005 |
| WO | 2006/099126 A2 | 9/2006 |
| WO | 2008/089795 A1 | 7/2008 |
| WO | 2008/097461 A2 | 8/2008 |
| WO | 2009/044284 A1 | 4/2009 |
| WO | 2009/139822 A1 | 11/2009 |

OTHER PUBLICATIONS

Kemna, E.H., et al., "Hepcidin: from discovery to differential diagnosis," Haematologica 93(1):90-97 (2008).
Gutierrez, J.A., et al., "Quantitative determination of peptides using matrix-assisted laser desorption/ionization time-of-flight mass spectrometry," BioTechniques 38:S13-S17 (2005).
Murphy, et al., "Quantitation of hepcidin from human and mouse serum using liquid chromatography tandem mass spectrometry," Blood 110:1048-1054 (2007).
Kemna, E.H., et al., "Mass Spectrometry-Based Hepcidin Measurement in Serum and Urine: Analytical Aspects and Clinical Implications," Clinical Chemistry 53:620-628 (2007).
Tomosugi, N., et al., "Detection of serum hepcidin in renal failure and inflammation by using ProteinChip System," Blood 108(4):1381-1387 (2006).
Koliaraki, V., et al., "A novel immunological assay for hepcidin quantification in human serum," Plos One 4(2):e4581 (2009).
Alpha Diagnostic International, Product Specification Sheet, Catalog #HEPC11-S, HEPC11-A, HEPC11-P, www.4adi.com, (2008).
Alpha Diagnostic International, Product Specification Sheet, Catalog # HEPC12-S, HEPC12-a, HEPC12-P, www.4adi.com, (2008).
Alpha Diagnostic International, Product Specification Sheet, Catalog # HEPC13-S, HEPC13-a, HEPC13-P, www.4adi.com, (2008).
DRG Hepcidin Prohormone ELISA (EIA-4644) corp@drg-international.com, pp. 1-10 (2007).
Kemna, et al., "Measuring serum hepcidin concentrations," Nature Clinical Practice Gastroenterology & Hepatology 2: E1 (2005).
Nemeth, E., et al., "Hepcidin, a putative mediator of anemia of inflammation, is a type II acute-phase protein," Blood 101(7):2461-2463 (2003).
Nicolas, G., et al., "Lack of hepcidin gene expression and sever tissue iron overload in upstream stimulatory factor 2 (USF2) knockout mice," PNAS 98(15):8780-8785 (2001).
Roe, M., et al., "Serum prohepcidin concentration: no association with iron absorption in healthy men; and no relationship with iron status in men carrying HFE mutations, hereditary haemochromatosis patients undergoing phlebotomy treatment, or pregnant women," British Journal of Nutrition 97:544-549 (2007).
Valore, E., et al., "Posttranslational processing of hepcidin in human hepatocytes is mediated by the prohormone convertase furin," Blood Cells, Molecules and Diseases 40:132-138 (2008).

*Primary Examiner* — Sheela J Huff
(74) *Attorney, Agent, or Firm* — Robert L. Sharp

(57) ABSTRACT

Monoclonal antibodies are provided that selectively bind human hepcidin-25 and are characterized as having high affinity for human hepcidin-25 and strong human mature hepcidin neutralizing properties. The antibodies of the invention are useful therapeutically for increasing serum iron levels, reticulocyte count, red blood cell count, hemoglobin, and/or hematocrit in a human and for the treatment and diagnosis of mature hepcidin-promoted disorders such as anemia, in a human subject.

5 Claims, 5 Drawing Sheets

Peaks:
1. Hepcidin-25: MW 2790
2. Hepcidin-24: MW 2674
3. Hepcidin-22: MW 2436
4. Hepcidin-20: MW 2192

Peaks:
1. Hepcidin-25 (25aa): MW 2790
2. Pro-hepcidin (60aa): MW 6929

A. Amino acid sequence of human light chain framework
O2 with interspersed CDR residues

FRL1 (SEQ ID NO: 39)        FRL2 (SEQ ID NO: 40)
                              LCDR1                   LCDR2
DIQMTQSPSSLSASVGDRVTITCXXXXXXXXXXXXWYQQKPGKAPKLLIYXXXXXXX

FRL3 (SEQ ID NO: 96)        FRL4 (SEQID NO:97)
                                    LCDR3
GVPSRFSGSGSGTDFTLTISSLQPEDFATYYCXXXXXXXXXFGGGTKVEIK

B. Amino acid sequence of a human heavy chain framework
VH1-69 with interspersed CDR residues

FRH1 (SEQ ID NO: 35)        FRH2 (SEQ ID NO: 36)
                                  HCDR1
QVQLVQSGAEVKKPGSSVKVSCKASXXXXXXXXXXXWVRQAPGQGLEWMG

FRH3 (SEQ ID NO: 37)
  HCDR2
XXXXXXXXXXXXXXXXXRVTITADKSTSTAYMELSSLRSEDTAVYYCAR

FRH4 (SEQ ID NO: 38)
  HCDR3
XXXXXXXXWGQGTTVTVSS

FIGURE 3

A. Amino acid sequence of human light chain framework O18 with interspersed CDR residues

```
     FRL1 (SEQ ID NO: 154)          FRL2 (SEQ ID NO: 40)
                           LCDR1                        LCDR2
DIQMTQSPSSLSASVGDRVTITCXXXXXXXXXXXXWYQQKPGKAPKLLIYXXXXXXX

FRL3 (SEQ ID NO: 156)           FRL4 (SEQ ID
NO:97)
                                  LCDR3
GVPSRFSGSGSGTDFTFTISSLQPEDIATYYCXXXXXXXXXFGGGTKVEIK
```

B. Amino acid sequence of a human heavy chain framework VH1-18 with interspersed CDR residues

```
       FRH1 (SEQ ID NO: 157)    FRH2 (SEQ ID NO: 36)
                          HCDR1
QVQLVQSGAEVKKPGASVKVSCKASXXXXXXXXXXXWVRQAPGQGLEWMG

FRH3 (SEQ ID NO: 158)
    HCDR2
XXXXXXXXXXXXXXXXXRVTMTDSTSTAYMELRSLRSDDTAVYYCAR

FRH4 (SEQ ID NO: 38)
  HCDR3
XXXXXXXWGQGTTVTVSS
```

Residues different from O2 residues are bold and underlined

FIGURE 4

A. Amino acid sequence of human light chain framework L12 with interspersed CDR residues FRL1 (SEQ ID NO: 159)      FRL2 (SEQ ID NO: 40)
                            LCDR1                  LCDR2
DIQMTQSPSTLSASVGDRVTITCXXXXXXXXXXXXWYQQKPGKAPKLLIYXXXXXXX FRL3 (SEQ ID NO: 160)      FRL4 (SEQ ID NO:97)
                                   LCDR3
GVPSRFSGSGSGTEFTLTISSLQPDDFATYYCXXXXXXXXXFGGGTKVEIK B. Amino acid sequence of a human heavy chain framework VH1-46 with interspersed CDR residues FRH1 (SEQ ID NO: 157)    FRH2 (SEQ ID NO: 36 )
                              HCDR1
QVQLVQSGAEVKKPGASVKVSCKASXXXXXXXXXXXXWVRQAPGQGLEWMG FRH3 (SEQ ID NO: 161)
  HCDR2
XXXXXXXXXXXXXXXXXRVTMTRDTSTSTVYMELSSLRSEDTAVYYCAR

FRH4 (SEQ ID NO: 38)
  HCDR3
XXXXXXXXWGQGTTVTVSS

Residues different from O2 residues are bold and underlined

FIGURE 5

ANTI-HEPCIDIN ANTIBODIES AND USES THEREOF

This application is a continuation of U.S. patent application Ser. No. 12/872,172, filed 31 Aug. 2010, now U.S. Pat. No. 8,329,174, which is a continuation of U.S. patent application Ser. No. 12/260,125, filed 29 Oct. 2008, now U.S. Pat. No. 7,820,163, which claims the priority under 35 U.S.C. §119(e) of U.S. Provisional Application No. 60/984,910, filed 2 Nov. 2007.

The present invention is in the field of medicine, particularly in the field of antibodies against human mature hepcidin. More specifically, the invention relates to hepcidin-25 selective monoclonal antibodies which are capable of neutralizing human mature hepcidin bioactivity and, therefore, are useful for increasing serum iron levels, reticulocyte count, red blood cell count, hemoglobin, and/or hematocrit in a human for purposes of treating or preventing a human mature hepcidin-promoted disease, condition, or disorder such as anemia.

Presently, suitable and effective therapies for anemia, or for anemia of chronic disease, are limited. Specifically, erythropoietin administration is effective in only about 50% of all the patients, and is associated with undesirable side effects. Furthermore, transfusions are undesirable due to the risks of contamination, infection, and iron overload.

Human hepcidin, a polypeptide expressed predominantly by hepatocytes, is believed to be an important iron-regulating protein that negatively regulates intestinal iron absorption, iron recycling by macrophages, and iron mobilization from hepatic iron stores. Overproduction of hepcidin appears to play a primary role in the pathophysiology of anemia and/or anemia of chronic disease.

Human hepcidin is encoded as an 84-amino acid prepropeptide containing a typical N-terminal 24-amino acid endoplasmic reticulum-targeting signal sequence, and a 35-amino acid proregion with a consensus furin-cleavage site immediately followed by the C-terminal 25 amino acid bioactive iron-regulatory hormone, human hepcidin-25 (SEQ ID NO: 1). Various N-terminal truncated forms of human hepcidin-25, such as human hepcidin-20 (i.e., amino acids 6-25 of SEQ ID NO: 1) and human hepcidin-22 (amino acids 4-25 of SEQ ID NO: 1) are also known to form in vivo.

Although antibodies to human hepcidin have been reported previously (see, e.g., U.S. Patent Application Publications 2004/0096990 and 2007/0224186, and PCT International Patent Application Publication WO 2008/097461), there still remains a great need in the art for additional drugs to treat diseases and disorders associated with anemia including anemia of chronic disease such as anemia of cancer and anemia of inflammation. Because hepcidin-25 is the most, if not the only, physiologically relevant form of hepcidin in humans, antibodies that selectively target human hepcidin-25 as compared to hepcidin polypeptides that are not physiologically relevant, are particularly needed. Therefore, the present invention provides selective, high affinity, engineered therapeutic antibodies against human hepcidin-25 that have numerous advantages in the treatment or diagnosis of disorders associated with elevated levels of mature hepcidin such as anemia. For example, these antibodies, being high affinity, neutralizing, human engineered and highly selective for physiologically relevant forms of hepcidin in humans, will reduce the risk for side-effects and the clinical dose and frequency of dosing required for effective treatment. The present invention also includes preferred nucleic acids encoding preferred selective hepcidin-25 antibodies wherein the nucleic acids have been engineered to remove cryptic splice sites that result in undesirable aggregation of certain antibodies of the invention upon expression by mammalian host cells. Thus, additional benefits derived from this the present invention include improved yield of the antibody product of a desirable degree of purity, thereby cutting costs of production, as well as a greater degree of clinical effectiveness and safety for the antibody product administered.

Furthermore, commercially available immunoassays for human hepcidin do not differentiate the active, physiologically relevant forms of human hepcidin from inactive, physiologically non-relevant hepcidin species (see, for example, Kemna, E. H., et al., Haematologica, 93(1):90-7 (2008)). Presently, most methods to selectively assay for hepcidin-25 involve LC/MS (liquid chromatography/mass spectroscopy) or similar cumbersome methods which require the separation of the various forms of hepcidin (see, for example, (Gutierrez, J. A., et al., BioTechniques, 38:S13-S17 (2005), Murphy, et al., Blood, 110:1048-54 (2007) and Kemna, E. H., et al., Clin. Chem. 53:620-8 (2007)). While these assays may be accurate and precise, their complexity, expense, and the high level of operator expertise required inhibit their routine implementation. Accordingly, there is also a great need for additional antibodies that bind human mature hepcidin with high affinity for their application in relatively simple, rapid, and robust immunoassay for the specific detection or measurement of mature forms of human hepcidin for diagnostic and/or prognostic applications.

The present invention provides antibodies that bind human hepcidin-25 with a binding affinity ($K_D$) of about 800 pM or less as determined by surface plasmon resonance (SPR) at 25° C. Preferably, the antibody has a dissociation rate ($k_{off}$) for human hepcidin-25 between about $8.5 \times 10^{-3}$ s$^{-1}$ and about $1.8 \times 10^{-4}$ s$^{-1}$ as determined by SPR at 25° C. More preferably, the antibody has a $K_D$ for human hepcidin-25 between about 400 pM to about 30 pM as determined by SPR at 25° C. Even more preferably, the antibody has a $K_D$ for human hepcidin-25 between about 200 pM to about 30 pM as determined by SPR at 25° C. Even more preferably, the antibody has an IC$_{50}$ between about 100 nM and about 25 nM in an in vivo assay of hepcidin-25 bioactivity, preferably, wherein the assay measures an IL-6-induced decrease in serum iron levels. Even more preferably, the antibody has an IC$_{50}$ between about 100 nM and about 50 nM in an in vitro assay of hepcidin-25 bioactivity, preferably, wherein the assay measures hepcidin-induced internalization and/or degradation of ferroportin. Even more preferably, the antibodies comprise at least one of the CDRs selected from the group consisting of i) a HCDR3 having the amino acid sequence as shown in SEQ ID NO: 75, and ii) a LCDR3 having the amino acid sequence as shown in SEQ ID NO: 62.

The present invention includes an antibody that selectively binds human hepcidin-25 with a $K_D$ of about 800 pM or less and comprises a heavy chain variable region ("HCVR") polypeptide and a light chain variable region ("LCVR") polypeptide wherein (i) the HCVR and the LCVR polypeptides have the amino acid sequences as shown in SEQ ID NOs: 148 and 126, respectively; (ii) the HCVR and the LCVR polypeptides have the amino acid sequences as shown in SEQ ID NOs: 128 and 127, respectively; (iii) the HCVR and the LCVR polypeptides have the amino acid sequences as shown in SEQ ID NOs: 151 and 125, respectively; or (iv) the HCVR and the LCVR polypeptides have the amino acid sequences as shown in SEQ ID NOs: 150 and 124, respectively.

The present invention includes an antibody that selectively binds human hepcidin-25 with a $K_D$ of about 800 pM or less and comprises a heavy chain polypeptide and a light chain polypeptide wherein (i) the heavy chain and light chain polypeptides have the amino acid sequences as shown in SEQ ID NOs: 6 and 14, respectively; (ii) the heavy chain and light chain polypeptides have the amino acid sequences as shown in SEQ ID NOs: 7 and 15, respectively; (iii) the heavy chain and light chain polypeptides have the amino acid sequences as shown in SEQ ID NOs: 9 and 17, respectively; or (iv) the heavy chain and light chain polypeptides have the amino acid sequences as shown in SEQ ID NOs: 8 and 16, respectively.

The present invention includes an antibody that selectively binds human hepcidin-25 with a $K_D$ of about 800 pM or less and comprises a LCVR polypeptide comprising 3 CDR sequences which are present together in a Fab listed in Table 1 herein and which are present in the antibody in the same CDR position as shown in Table 1. Preferably, such an antibody comprises a LCVR polypeptide having an amino acid sequence selected from the group consisting of SEQ ID NOs: 101-127.

The present invention includes an antibody that selectively binds human hepcidin-25 with a $K_D$ of about 800 pM or less and comprises a HCVR polypeptide comprising 3 CDR sequences which are present together in a Fab listed in Table 2 herein and which are present in the antibody in the same CDR position as shown in Table 2. Preferably, such an antibody comprises a HCVR polypeptide having an amino acid sequence selected from the group consisting of SEQ ID NOs: 128-151.

The present invention includes an antibody that selectively binds human hepcidin-25 with a $K_D$ of about 800 pM or less and comprises i) a LCVR polypeptide comprising 3 CDRs which are present together in a Fab listed in Table 1 and which are present in the antibody in the same CDR position as shown in Table 1, and ii) a HCVR polypeptide comprising 3 CDRs which are present together in a Fab listed in Table 2 and which are present in the antibody of the invention in the same CDR position as shown in Table 2. Preferably, such an antibody comprises 6 CDRs which are present together in a Fab listed in Table 3 herein and which are present in the antibody in the same CDR position as shown in Table 3.

The present invention includes an antibody that selectively binds human hepcidin-25 with a $K_D$ of about 200 pM or less and comprises (i) a LCVR polypeptide having an amino acid sequence selected from the group consisting of SEQ ID NOs: 101-127, and (ii) a HCVR polypeptide having an amino acid sequence selected from the group consisting of SEQ ID NOs: 128-151.

The present invention also includes an antibody that selectively binds human hepcidin-25 with a $K_D$ of about 200 pM or less and comprises two heavy chain polypeptides and two light chain polypeptide, and wherein each of the heavy chain polypeptides have the amino acid sequence as shown in SEQ ID NO: 8 and each of the light chain polypeptides have the amino acid sequence as shown in SEQ ID NO: 16.

In other aspects, the invention provides isolated nucleic acid molecules encoding antibodies of the invention; vectors comprising nucleic acid molecules encoding antibodies of the invention, optionally, operably-linked to control sequences recognized by a host cell transformed with the vector; host cells comprising vectors comprising nucleic acid molecules encoding antibodies of the invention; a process for producing an antibody of the invention comprising culturing host cells comprising vectors comprising nucleic acid molecules encoding antibodies of the invention so that the nucleic acid is expressed and, optionally, recovering the antibody from the host cell culture medium.

In another aspect, the invention provides a pharmaceutical composition comprising an antibody of the invention and a pharmaceutically acceptable carrier or diluent. Preferably, the pharmaceutical composition comprises a homogeneous or substantially homogeneous population of an antibody of the invention and a pharmaceutically acceptable carrier or diluent.

In another embodiment, the invention provides an antibody that selectively binds human hepcidin-25 with a $K_D$ of about 800 pM or less for use in therapy. The invention also provides an antibody that selectively binds human hepcidin-25 with a $K_D$ of about 800 pM or less for use in treating or preventing anemia in a subject.

The present invention includes the use of an antibody that selectively binds human hepcidin-25 with a $K_D$ of about 800 pM or less for the preparation of a medicament for the treatment of anemia, including anemia of chronic disease and anemia of cancer. The invention further includes the use of an antibody that selectively binds human hepcidin-25 with a $K_D$ of about 800 pM or less for the preparation of a medicament for increasing serum iron levels, reticulocyte count, red blood cell count, hemoglobin, and/or hematocrit in an animal, preferably a mammalian species, more preferably a human subject.

The present invention includes a method of increasing serum iron levels, reticulocyte count, red blood cell count, hemoglobin, and/or hematocrit that comprises administering to a human subject in need thereof, an effective amount of an antibody that selectively binds human hepcidin-25 with a $K_D$ of about 800 pM or less.

In another aspect, the invention provides a method for treating in a patient a mature hepcidin-promoted disorder which benefits from an increase in serum iron levels, reticulocyte count, red blood cell count, hemoglobin, and/or hematocrit, including, but not limited to, anemia, e.g., anemia resulting from infection, inflammation, chronic disease, and/or cancer wherein said method comprises administering an effective amount of a hepcidin-25 selective antibody of the invention to a patient in need thereof.

The present invention further provides an immunoassay selective for human mature hepcidin. The method includes: first, obtaining a sample to be assayed for human mature hepcidin and contacting the sample with an antibody of the invention under suitable conditions for binding and allowing any human mature hepcidin present to form an antigen-antibody complex; then detecting the presence or absence of the complex; and/or determining the amount of the complex in the sample by an immunoassay method.

The present invention further provides methods of diagnosing a human mature hepcidin-promoted condition in a patient by determining the level of human mature hepcidin in a sample of a biological fluid from the patient and comparing the level of human mature hepcidin in the sample with the level of human mature hepcidin in a sample of biological fluid from one or more control individuals or with a reference standard.

A method of monitoring a mature hepcidin-promoted disorder in a patient is also provided. The method includes determining the level of mature hepcidin in a sample of a biological fluid from a patient suffering from, or at risk of, a mature hepcidin-promoted disorder at a first time point; determining the level of mature hepcidin in one or more samples of the biological fluid from the patient at one or more different time points; comparing the levels of mature hepcidin determined at different time points and thereby monitoring the mature hepcidin-promoted disorder. The invention further provides a kit for performing an immunoassay, including an antibody of the invention and a suitable container.

Figure 1:
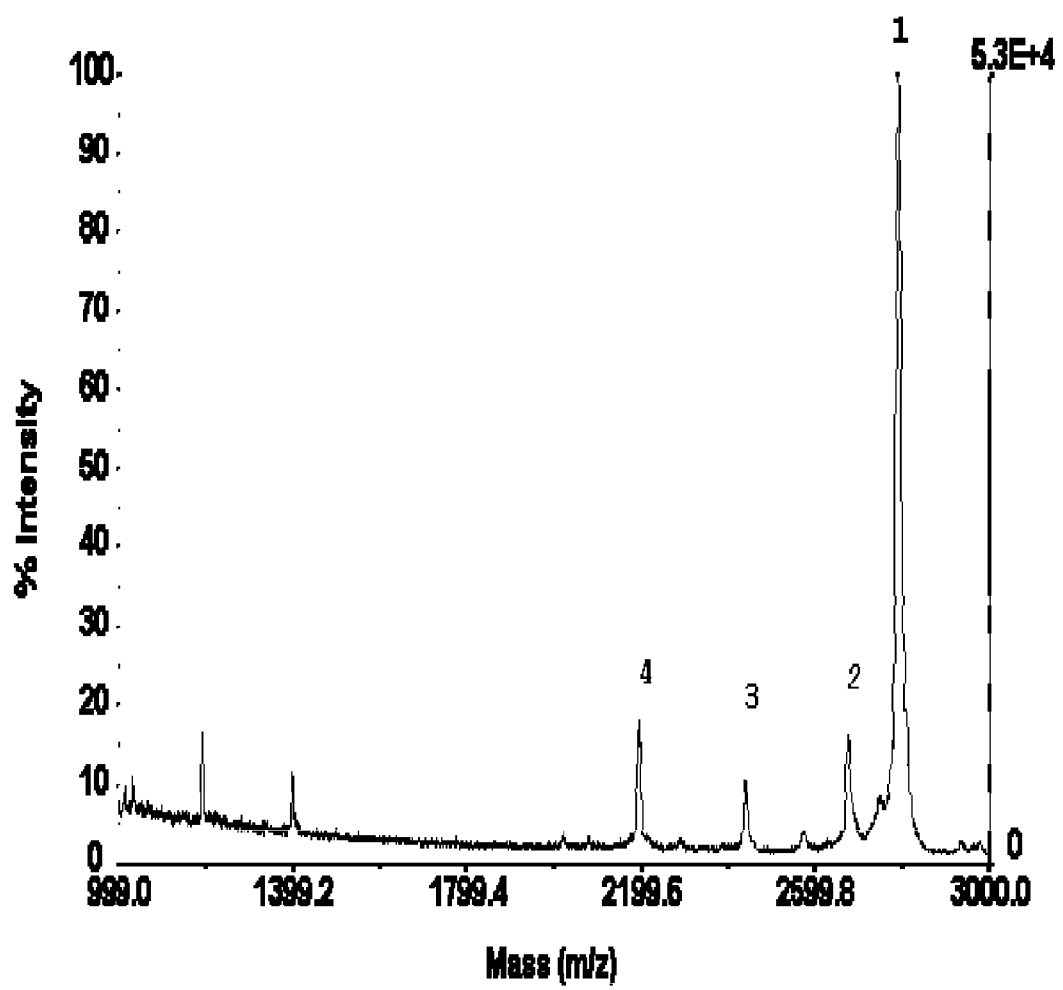
FIG. 1 depicts a MALDI-TOF mass spectrum of multiple forms of human hepcidin isolated from human sera. Signal 1 has a mass which is consistent with the expected mass of intact human hepcidin-25. Signals 2, 3, and 4 have masses that are consistent with N-terminally truncated forms of human mature hepcidin (hepcidin-24, hepcidin-22, and hepcidin-20). The mass spectrum was generated on a MALDI-TOF mass spectrometer utilizing a positive ion, linear mode method with a-cyano-4- hydroxycinnamic acid (peptide matrix) as sample matrix as described in Example 5 below.
Figure 2:
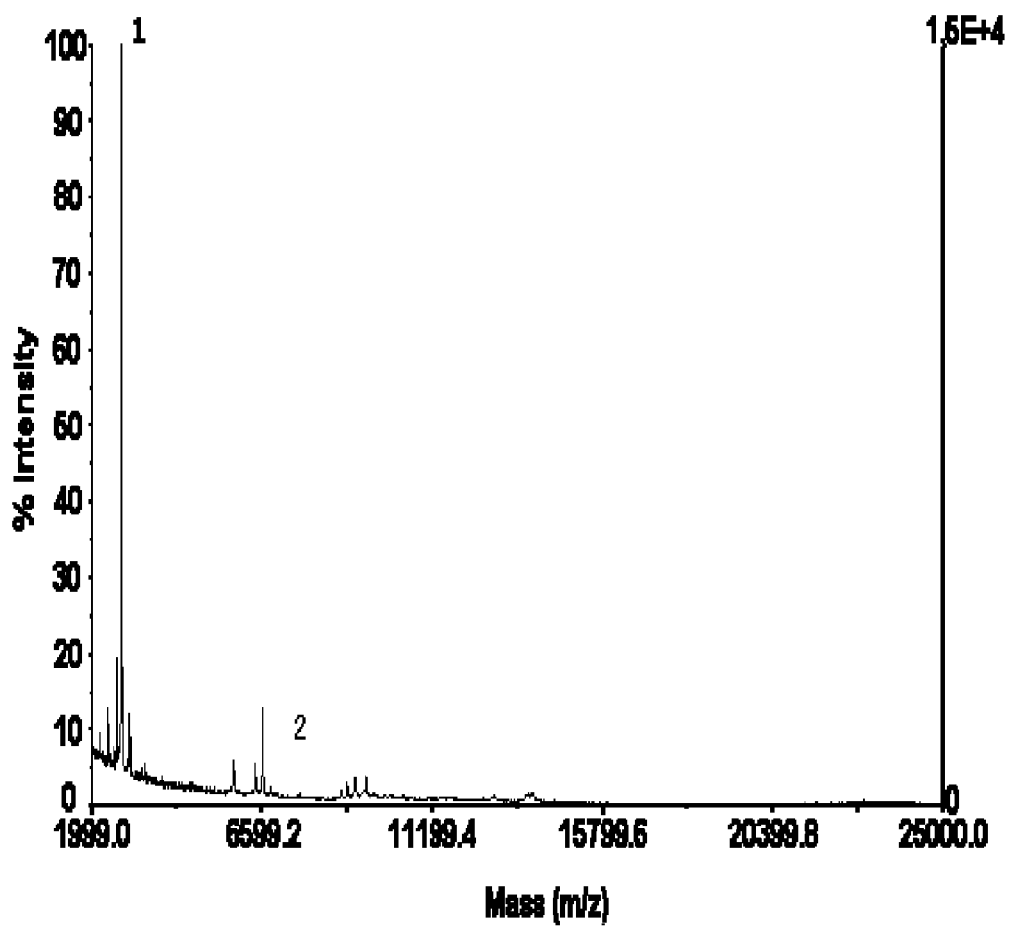

FIG. 2 depicts a MALDI-TOF mass spectrum of the same sample as in FIG. 1 using 3,5-dimethyl-4 hydroxycinnamic acid (sinapinic acid matrix) as sample matrix. Signal 1 represents intact human hepcidin-25. No signal for pro-hepcidin was observed. The mass spectrum was generated on a mass spectrometer utilizing a positive ion, linear mode method as described in Example 5 below.

FIG. 3A shows the amino acid sequences of fully human light chain framework O2 with interspersed CDRs. The four framework regions are labeled as FRL1, 2, 3, and 4 (SEQ ID NOs: 39, 40, 96, and 97, respectively).

FIG. 3B shows the amino acid sequence of the human heavy chain framework VH1-69 with interspersed CDRs. The four framework regions are labeled FRH1-4 (SEQ ID NOs: 35-38, respectively).

FIG. 4A shows the amino acid sequences of the human light chain framework O18 with interspersed CDRs The four framework regions are labeled as FRL1, 2, 3, and 4 (SEQ ID NOs: 154, 40, 156, and 97, respectively).

FIG. 4B shows the amino acid sequence of the human heavy chain framework VH1-18 with interspersed CDRs. The four framework regions are labeled FRH1, 2, 3, and 4 (SEQ ID NOs: 157, 36, 158, and 38, respectively).

FIG. 5A shows the amino acid sequences of the human light chain framework L12 with interspersed CDRs The four framework regions are labeled as FRL1, 2, 3, and 4 (SEQ ID NOs: 159, 40, 160, and 97, respectively).

FIG. 5B shows the amino acid sequence of the human heavy chain framework VH1-46 with interspersed CDRs. The four framework regions are labeled FRH1, 2, 3, and 4 (SEQ ID NOs: 157, 36, 161, and 38, respectively).

The following abbreviations are used herein: ACN: acetonitrile, BSA: bovine serum albumin, DTT: dithiothreitol, EDTA: ethylenediamine tetraacetic acid, ELISA: enzyme linked immunosorbent assay, IMAC: immobilized metal-affinity chromatography, IPTG: isopropyl β-D-1-thiogalactopyranoside, Mab: monoclonal antibody, Mabs: monoclonal antibodies, MALDI-TOF: Matrix-Associated Laser Desorption Ionization-Time of Flight, PBS: phosphate-buffered saline, SPR: surface plasmon resonance, TFA: trifluoroacetic acid. All amino acid abbreviations used in this disclosure are those accepted by the United States Patent and Trademark Office as set forth in 37 C.F.R. §1.822 (B)(2).

When used herein, the term "hepcidin" refers to any form of the hepcidin protein known to be present in mammals. When used herein, the term "mature hepcidin" refers to any mature, bioactive form of the hepcidin protein expressed in mammals. When used herein, the phrase "human hepcidin" refers to any form of the hepcidin protein present in humans. When used herein, the phrase "human hepcidin-25" refers to the mature form of human hepcidin having the amino acid sequence as shown in SEQ ID NO: 1.

The term "antibody" in reference to an anti-hepcidin antibody of the invention (or simply, "antibody of the invention"), as used herein, refers to a human engineered monoclonal antibody or a fully human monoclonal antibody, unless otherwise indicated. Preferably, the antibodies of the invention are human engineered antibodies. Antibodies of the invention can be produced using e.g., recombinant technologies, phage display technologies, synthetic technologies, e.g., CDR-grafting, or combinations of such technologies or other technologies readily known in the art. "Monoclonal antibody" refers to an antibody that is derived from a single copy or clone, including e.g., any eukaryotic, prokaryotic, or phage clone, and not the method by which it is produced. An antibody as used herein can be an intact antibody (comprising a complete or full length Fc region), or a portion or fragment of an antibody comprising an antigen-binding portion, e.g., a Fab fragment, Fab' fragment, or F(ab')$_2$ fragment of a human engineered or fully human antibody. Preferred antigen-binding fragments of an antibody of the invention retain the ability to inhibit or neutralize one or more bioactivities characteristic of a mature form of a mammalian hepcidin in vivo or in vitro. For example, in one embodiment, an antigen-binding portion of an antibody of the invention can inhibit the interaction of human hepcidin-25 with one or more receptors, e.g., human ferroportin (SEQ ID NO: 25), and/or can inhibit hepcidin-induced internalization of ferroportin.

Furthermore, an "antibody of the invention" or simply "antibody" as used herein can be a single chain FIT fragment that may be produced by joining the DNA encoding the LCVR and HCVR with a linker sequence. (See, Pluckthun, *The Pharmacology of Monoclonal Antibodies*, vol. 113, Rosenburg and Moore eds., Springer-Verlag, N.Y., pp 269-315, 1994). It is understood that regardless of whether antigen-binding fragments or portions are specified, the term "antibody" as used herein includes such fragments or portions as well as single chain forms, unless indicated otherwise.

The terms "selective" or "selectively" used herein in reference to an anti-hepcidin-25 antibody or the binding thereof, respectively, refers to an antibody that selectively binds hepcidin-25 with a $K_D$ of about 1000-, 500-, 200-, 100-, 50-, 10-, or about 5-fold lower than the antibody binds at least one precursor form of hepcidin-25 and/or at least one N-terminally truncated species of mature hepcidin known to form in the same mammalian species, as measured by SPR at 25° C. Additionally, or alternatively, a hepcidin-25 selective antibody of the invention binds to hepcidin-25 but does not bind, or minimally binds, to at least one precursor form of hepcidin-25 and/or at least one N-terminally truncated species of mature hepcidin known to form in the same mammalian species as determined by immunoassay and/or MALDI-TOF mass spectrometry methods used by those skilled in the art including, but not limited to, the assay described in Example 5 herein. Preferably, an anti-hepcidin-25 selective antibody of the present invention binds human hepcidin-25 with a $K_D$ of about 1000-, 500-, 200-, 100-, 50-, 10-, or about 5-fold lower than the antibody binds human pro-hepcidin, preferably, human pro-hepcidin having the amino acid sequence shown in SEQ ID NO: 34, and/or at least one N-terminally truncated form of human mature hepcidin, as measured by SPR at 25° C. Additionally, or alternatively, an anti-hepcidin-25 selective antibody of the invention binds to human hepcidin-25 but does not bind, or minimally binds, to human pro-hepcidin, preferably, the human pro-hepcidin having the amino acid sequence shown in SEQ ID NO: 34, and/or at least one N-terminally truncated species of mature hepcidin known to form in the same mammalian species as determined by immunoassay and/or MALDI-TOF mass spectrometry methods used by those skilled in the art including, but not limited to, the assay described in Example 5 herein. More preferably, an anti-hepcidin-25 selective antibody of the present invention binds human hepcidin-25 with a $K_D$ of about 1000-, 500-, 200-, 100-, 50-, 10-, or about 5-fold lower than the antibody binds human pro-hepcidin having the amino acid sequence shown in SEQ ID NO: 34 and at least one N-terminally truncated form of human mature hepcidin, as measured by SPR at 25° C. Additionally, or alternatively, an anti-hepcidin-25 selective antibody of the invention binds to human hepcidin-25 but does not bind, or minimally binds, to human pro-hepcidin (SEQ ID NO: 34), and at least one N-terminally truncated species of mature hepcidin known to form in the same mammalian species as determined by immunoassay and/or MALDI-TOF mass spectrometry methods used by those skilled in the art including, but not limited to, the assay described in Example 5 herein. Most preferably, an anti-hepcidin-25 selective antibody of the present invention i) binds human hepcidin-25 with a $K_D$ of about 1000-, 500-, 200-, 100-, 50-, 10-, or about 5-fold lower than the antibody binds human pro-hepcidin (SEQ ID NO: 34) and ii) binds human hepcidin-25 with a $K_D$ of about 1000-, 500-, 200-, 100-, 50-, 10-, or about 5-fold lower than the antibody binds human hepcidin-20 (i.e., amino acids 6-25 of SEQ ID NO: 1) and/or human hepcidin-22 (amino acids 4-25 of SEQ ID NO: 1), as measured by SPR at 25° C. Additionally, or alternatively, an anti-hepcidin-25 selective antibody of the invention binds to human hepcidin-25 but does not bind, or minimally binds, to i) human pro-hepcidin (SEQ ID NO: 34) and ii) human hepcidin-20 and/or human hepcidin-22, as determined by immunoassay and/or MALDI-TOF mass spectrometry methods used by those skilled in the art including, but not limited to, the assay described in Example 5 herein.

The term "detect" or "detecting" is used in the broadest sense to include quantitative, semi-quantitative or qualitative measurements of a target molecule. In one aspect, methods described herein may only determine the presence or absence of a particular hepcidin polypeptide in a biological sample and, thus, that the hepcidin polypeptide is detectable or, alternatively, undetectable in the sample as determined by the method.

The term "epitope" refers to that portion of a molecule capable of being recognized by and bound by an antibody at one or more of the antibody's antigen-binding regions.

The term "bioactivity," in reference to an antibody of the invention, includes, but is not limited to, epitope or antigen binding affinity, the in vivo and/or in vitro stability of the antibody, the immunogenic properties of the antibody, e.g., when administered to a human subject, and/or the ability to neutralize or antagonize a bioactivity of hepcidin, in vivo or in vitro, including, but not limited to, inhibition of serum iron level dysregulation in an inflammation, e.g., IL-6, challenge assay, e.g., as described in Example 4 herein. The aforementioned properties or characteristics can be observed or measured using art-recognized techniques including, but not limited to, scintillation proximity assays, ELISA, ORIGEN immunoassay (IGEN), fluorescence quenching, fluorescence ELISA, competitive ELISA, SPR analysis including, but not limited to, SPR analysis using a BIAcore biosenser, in vitro and in vivo neutralization assays without limit (see, for example, International Publication No. WO 2006/062685), receptor binding, and immunohistochemistry with tissue sections from different sources including human, primate, or any other source as the need may be.

The term "bioactivity" in reference to mature hepcidin including hepcidin-25 includes, but is not limited to, specific binding of mature hepcidin to another protein including, but not limited to, its receptor ferroportin, one or more ferroportin-mediated functions of mature hepcidin, such as mature hepcidin-induced internalization and/or degradation of ferroportin (see, e.g., Nemeth, E., et al., Hepcidin Regulates Iron Efflux by Binding to Ferroportin and Inducing Its Internalization, *Science* 306, 2090-2093, (2004)), mature hepcidin regulation of ferroportin-mediated iron efflux, serum iron levels, reticulocyte count, red blood cell count, hemoglobin, and/or hematocrit in a human, protein stability, i.e., mature hepcidin affecting the levels or activity of another protein in vivo or in vitro, and hepcidin expression levels and/or tissue distribution.

The term "inhibit" or "neutralize" as used herein with respect to a bioactivity of an antibody of the invention means the ability to substantially antagonize, prohibit, prevent, restrain, slow, disrupt, eliminate, stop, reduce or reverse a bioactivity of human mature hepcidin, including, but not limited to, a human mature hepcidin bioactivity as measured in Example 3 or 4 herein.

The antibodies of the present invention are characterized by having a $K_D$ for human hepcidin-25 less than about 1000 pM, preferably, less than about 800 pM, more preferably, less than about 400 pM, even more preferably, less than about 200 pM, even more preferably, less than about 100 pM, even more preferably, less than about 75 pM, or most preferably, less than about 50 pM, as determined by SPR at 25° C. Preferably, the antibody selectively binds human hepcidin-25 with a $K_D$ less than about 800 pM, preferably, less than about 400 pM, more preferably, less than about 200 pM, even more preferably, less than about 100 pM, even more preferably, less than about 75 pM, or most preferably, less than about 50 pM, as determined by SPR at 25° C. also selectively binds at least one hepcidin-25 of another species such as cynomolgous monkey hepcidin-25. More preferably, such antibodies selectively bind cynomolgous monkey hepcidin-25 with a $K_D$ less than about 800 pM, even more preferably, less than about 400 pM, even more preferably, less than about 200 pM, even more preferably, less than about 100 pM, even more preferably, less than about 75 pM, or most preferably, less than about 50 pM, as determined by SPR at 25° C.

The antibodies of the present invention include anti-hepcidin-25 selective antibodies having a $K_D$ for human hepcidin-25 between about 800 pM and about 30 pM, preferably, between about 400 pM and about 30 pM, more preferably, between about 200 μM and about 30 pM, even more preferably, between about 100 pM and about 30 pM, even more preferably, between about 75 pM and about 30 pM, or most preferably, between about 50 pM and about 30 pM, as determined by SPR at 25° C. Preferably, such antibodies also have a $K_D$ for cynomolgus monkey hepcidin-25 between about 800 pM and 10 pM, more preferably, between about 400 pM and about 10 pM, even more preferably, between about 200 pM and about 10 pM, even more preferably, between about 100 pM and about 10 pM, even more preferably, between about 75 pM and 10 pM, or most preferably, between about 50 pM and 10 pM, as determined by SPR at 25° C.

The antibodies of the present invention also include antibodies having a $K_D$ for human hepcidin-25 and/or cynomolgus monkey hepcidin-25 which is at least about 20-fold, at least about 30-fold, at least about 40-fold, at least about 50-fold, at least about 60-fold, at least about 70-fold, at least about 80-fold, at least about 90-fold, at least about 100-fold, or at least 200-fold less than the antibody's $K_D$ for mouse hepcidin-25 and/or rat hepcidin-25, as determined by SPR at 25° C.

The antibodies of the present invention also include antibodies having a $k_{off}$ rate from human hepcidin-25 between about $1 \times 10^{-2}$ s$^{-1}$ and about $1.8 \times 10^{-4}$ s$^{-1}$, preferably, between about $8.5 \times 10^{-3}$ s$^{-1}$ and about $1.8 \times 10^{-4}$ s$^{-1}$, more preferably, between about $7.7 \times 10^{-4}$ s$^{-1}$ and about $1.8 \times 10^{-4}$ s$^{-1}$, even more preferably, between about $6.5 \times 10^{-4}$ s$^{-1}$ and about $1.8 \times 10^{-4}$ s$^{-1}$, or most preferably, between about $5.5 \times 10^{-4}$ s$^{-1}$ and about $2.0 \times 10^{-4}$ s$^{-1}$, as determined by SPR at 25° C. Preferably, such an antibody also selectively binds human hepcidin-25 with a $K_D$ between about 800 pM and 30 pM, even more preferably, between about 400 pM and about 30 pM, even more preferably, between about 200 pM and about 30 pM, even more preferably, between about 100 pM and about 30 pM, even more preferably, between about 75 pM and 50 pM, or most preferably, between about 50 pM and 30 pM, as determined by SPR at 25° C.

The present invention also includes antibodies that bind human hepcidin-25, preferably, selectively, with a $K_D$ of about 200 pM or less and neutralizes or antagonizes at least one human mature hepcidin bioactivity in vitro or in vivo. Preferably, an antibody of the invention has an $IC_{50}$ lower than about 200 nM, more preferably, lower than about 100 nM, even more preferably, lower than about 75 nM, or most preferably, lower than about 50 nM in an in vitro or in vivo assay of mature hepcidin bioactivity as described, for example, in Example 3 or 4 herein.

An antibody of the invention also includes anti-human hepcidin-25 binding, preferably, selectively binding, antibodies that significantly inhibit IL-6-induced serum iron decreases in a cynomolgus monkey assay as described, for example, in Example 4 herein. Preferably, such antibodies inhibit serum iron decreases in a cynomolgus monkey induced by a 5 µg/kg dose of human IL-6 by at least about 30%, at least about 40%, at least about by 50%, at least about by 60%, at least about 70%, at least about 80%, at least about by 90%, or at least about by 100% within about 6 hours of receiving an intravenous dose of the antibody at about 10 mg/kg.

An antibody of the invention has an $IC_{50}$ lower than about 200 nM, preferably, less than about 100 nM, more preferably, less than about 75 nM, even more preferably, less than about 50 nM, or most preferably, less than about 25 nM in the mature hepcidin-induced ferroportin internalization assay described in Example 3 herein. Preferably, an antibody of the invention has an $IC_{50}$ between about 200 nM and about 25 nM, more preferably, between about 100 nM and about 50 nM, more preferably, between about 100 nM and about 25 nM, even more preferably, between about 75 nM and about 25 nM, or most preferably, between about 75 nM and about 50 nM in the mature hepcidin-induced ferroportin internalization assay described in Example 3 herein.

In another embodiment, an antibody of the invention has an $IC_{50}$ between about 200 nM and about 25 nM, preferably, between about 100 nM and about 50 nM, more preferably, between about 100 nM and about 25 nM, even more preferably, between about 75 nM and about 25 nM, or most preferably, between about 75 nM and about 50 nM in the hepcidin-induced ferroportin internalization assay described in Example 3, a $k_{off}$ rate from human hepcidin-25 between about $1 \times 10^{-2}$ s$^{-1}$ and about $1.8 \times 10^{-4}$ s$^{-1}$, preferably, between about $8.5 \times 10^{-3}$ s$^{-1}$ and about $1.8 \times 10^{-4}$ s$^{-1}$, more preferably, between about $7.7 \times 10^{-4}$ s$^{-1}$ and about $1.8 \times 10^{-4}$ s$^{-1}$, even more preferably, between about $6.5 \times 10^{-4}$ s$^{-1}$ and about $1.8 \times 10^{-4}$ s$^{-1}$, or most preferably, between about $5.5 \times 10^{-4}$ s$^{-1}$ and about $2.0 \times 10^{-4}$ s$^{-1}$, as determined by SPR at 25° C., and selectively binds human hepcidin-25 with a $K_D$ between about 800 pM and 30 pM, preferably, between about 400 pM and about 30 pM, more preferably, between about 200 pM and about 30 pM, even more preferably, between about 100 pM and about 30 pM, even more preferably, between about 75 pM and 50 pM, or most preferably, between about 50 pM and 30 pM, as determined by SPR at 25° C.

The term "Kabat numbering" as used herein is recognized in the art and refers to a system of numbering amino acid residues which are more variable (i.e., hypervariable) than other amino acid residues in the heavy and light chain regions of an antibody (Kabat, et al., *Ann. NY Acad. Sci.* 190:382-93 (1971); Kabat, et al., *Sequences of Proteins of Immunological Interest*, Fifth Edition, U.S. Department of Health and Human Services, NIH Publication No. 91-3242 (1991)).

A polynucleotide is "operably-linked" when it is placed into a functional relationship with another polynucleotide. For example, a promoter or enhancer is operably-linked to a coding sequence if it affects the transcription of the sequence.

The terms "subject" and "patient" used interchangeably herein, refer to a mammal, preferably, a human. In certain embodiments, the patient has a disorder that would benefit from a decreased level of hepcidin-25, a decrease in hepcidin-25 bioactivity, and/or an increase in serum iron level, reticulocyte count, red blood cell count, hemoglobin, and/or hematocrit, The term "vector" refers to a nucleic acid molecule capable of transporting another nucleic acid to which it has been operably-linked including, but not limited to, plasmids and viral vectors. Certain vectors are capable of autonomous replication in a host cell into which they are introduced while other vectors can be integrated into the genome of a host cell upon introduction into the host cell, and thereby, are replicated along with the host genome. Moreover, certain vectors are capable of directing the expression of genes to which they are operably-linked. Such vectors are referred to herein as "recombinant expression vectors" (or simply "expression vectors"). Exemplary vectors are well known in the art.

As used herein, the expressions "cell" and "host cell" are used interchangeably and refer to any prokaryotic cell (e.g., bacterial cells such as *E. coli*) or, preferably, eukaryotic cell (e.g., yeast cells, plant cells, insect cells, or mammalian cells such as CHO cells) whether located in vitro or in vivo. A host cell includes cells transformed, transduced, transfected, or infected with one or more recombinant expression vectors comprising a polynucleotide encoding an antibody of the invention. A host cell may be located in vitro or in vivo. For example, host cells may be located in a transgenic animal or a transgenic plant.

Each heavy chain of a full-length antibody is comprised of an N-terminal heavy chain variable region (herein "HCVR") and a C-terminal heavy chain constant region. Each light chain of a full-length antibody is comprised of an N-terminal light chain variable region (herein "LCVR") and a C-terminal light chain constant region. The HCVRs and LCVRs can be further subdivided into regions of hypervariability, termed complementarity determining regions ("CDRs"), interspersed with regions that are more conserved, termed framework regions ("FR"). The functional ability of an antibody to bind a particular antigen or epitope is largely influenced by the six CDRs present in the variable region of the antibody. Each HCVR and LCVR is composed of three CDRs (HCDR1, HCDR2 and HCDR3 in the HCVR and LCDR1, LCDR2 and LCDR3 in the LCVR) and four framework regions, arranged from amino-terminus to carboxy-terminus in the following order: FR1, CDR1, FR2, CDR2, FR3, CDR3, FR4.

Accordingly, the term "CDR" or "complementarity determining region" as used herein, is intended to mean the non-contiguous antigen combining sites found within the variable region of both heavy and light chain polypeptides. These particular regions have been described by Kabat, et al., J. Biol. Chem. 252, 6609-6616 (1977), Kabat, et al., Sequences of protein of immunological interest, (1991), and by Chothia, et al., J. Mol. Biol. 196:901-917 (1987) and by MacCallum, et al., J. Mol. Biol., 262:732-745 (1996) where the definitions include overlapping or subsets of amino acid residues when compared against each other. In the present disclosure, the assignment of amino acids to each domain is in accordance with well-known conventions (e.g., Kabat, (1991) and/or Chothia (1987)). The CDRs contain most of the residues which form specific interactions with the antigen.

Tables 1 and 2 below depict the amino acid sequences and consensus amino acid sequences encoding preferred CDRs for antibodies of the present invention.

TABLE 1

| Fab | LCDR1 | LCDR2 | LCDR3 |
|---|---|---|---|
| JXB7 | SASSSVSSTYLH (SEQ ID NO: 26) | RTSTLAS (SEQ ID NO: 30) | QQWSGYPFT (SEQ ID NO: 31) |
| 31B2 | SASSSVSSTYLH (SEQ ID NO: 26) | RTSTLAS (SEQ ID NO: 30) | QQWSGYPFT (SEQ ID NO: 31) |
| Hu22 | SASSRVSSTYLF (SEQ ID NO: 43) | RTSTLAS (SEQ ID NO: 30) | QQWSGYPFT (SEQ ID NO: 31) |
| 1 | SLSSRVSSTYLF (SEQ ID NO: 47) | RTSTLAS (SEQ ID NO: 30) | QQWSGYPFT (SEQ ID NO: 31) |
| 2 | SISSRVSSTYLF (SEQ ID NO: 48) | RTSTLAS (SEQ ID NO: 30) | QQWSGYPFT (SEQ ID NO: 31) |
| 3 | SWSSRVSSTYLF (SEQ ID NO: 49) | RTSTLAS (SEQ ID NO: 30) | QQWSGYPFT (SEQ ID NO: 31) |
| 4 | SAGSRVSSTYLF (SEQ ID NO: 50) | RTSTLAS (SEQ ID NO: 30) | QQWSGYPFT (SEQ ID NO: 31) |
| 5 | SASSRVVSTYLF (SEQ ID NO: 51) | RTSTLAS (SEQ ID NO: 30) | QQWSGYPFT (SEQ ID NO: 31) |
| 6 | SASSRVSSTYLF (SEQ ID NO: 43) | RTSPLAS (SEQ ID NO: 53) | QQWSGYPFT (SEQ ID NO: 31) |
| 7 | SASSRVSSTYLF (SEQ ID NO: 43) | RTSALAS (SEQ ID NO: 54) | QQWSGYPFT (SEQ ID NO: 31) |
| 8 | SASSRVSSTYLF (SEQ ID NO: 43) | RTSWLAS (SEQ ID NO: 55) | QQWSGYPFT (SEQ ID NO: 31) |
| 9 | SASSRVSSTYLF (SEQ ID NO: 43) | RTSTGAS (SEQ ID NO: 56) | QQWSGYPFT (SEQ ID NO: 31) |
| 10 | SASSRVSSTYLF (SEQ ID NO: 43) | RTSTLTS (SEQ ID NO: 57) | QQWSGYPFT (SEQ ID NO: 31) |
| 11 | SASSRVSSTYLF (SEQ ID NO: 43) | RTSTLVS (SEQ ID NO: 58) | QQWSGYPFT (SEQ ID NO: 31) |
| 12 | SASSRVSSTYLF (SEQ ID NO: 43) | RTSTLLS (SEQ ID NO: 59) | QQWSGYPFT (SEQ ID NO: 31) |
| 13 | SASSRVSSTYLF (SEQ ID NO: 43) | RTSTLAS (SEQ ID NO: 30) | QQWSGYPFV (SEQ ID NO: 61) |
| *Consensus | $SX_1X_2SX_3VSSTYLF$ (SEQ ID NO: 52) | $RTSX_4X_5X_6S$ (SEQ ID NO: 60) | $QQWSGYPFX_7$ (SEQ ID NO: 62) |

*$X_1$ is A, L, I, or W; $X_2$ is S or G; $X_3$ is R or S; $X_4$ is T, P, A, or W; $X_5$ is L or G; $X_6$ is A, T, V, or L; $X_7$ is T or V

TABLE 2

| Fab | HCDR1 | HCDR2 | HCDR3 |
|---|---|---|---|
| JXB7 | GYTFTIYPIE (SEQ ID NO: 27) | NFHPYNGDTNYNEKFKG (SEQ ID NO: 28) | GGTGSFDY (SEQ ID NO: 46) |
| 31B2 | GYTFYIYPIS (SEQ ID NO: 29) | NFHPYKGLTNYNEKFKG (SEQ ID NO: 33) | GGTGSFDY (SEQ ID NO: 46) |
| Hu22 | GYTFTIYPIS (SEQ ID NO: 32) | NFHPYLGDTNYNEKFKG (SEQ ID NO: 44) | GGTGSFDY (SEQ ID NO: 46) |
| 14 | GYTFLIYPIS (SEQ ID NO: 63) | NFHPYLGDTNYNEKFKG (SEQ ID NO: 44) | GGTGSFDY (SEQ ID NO: 46) |
| 15 | GYTFWIYPIS (SEQ ID NO: 64) | NFHPYLGDTNYNEKFKG (SEQ ID NO: 44) | GGTGSFDY (SEQ ID NO: 46) |
| 16 | GYTFTIYPIS (SEQ ID NO: 32) | NFHPYLGTTNYNEKFKG (SEQ ID NO: 66) | GGTGSFDY (SEQ ID NO: 46) |
| 17 | GYTFTIYPIS (SEQ ID NO: 32) | NFHPYLGLTNYNEKFKG (SEQ ID NO: 67) | GGTGSFDY (SEQ ID NO: 46) |
| 18 | GYTFTIYPIS (SEQ ID NO: 32) | NFHPYLGVTNYNEKFKG (SEQ ID NO: 68) | GGTGSFDY (SEQ ID NO: 46) |
| 19 | GYTFTIYPIS (SEQ ID NO: 32) | NFHPYLGMTNYNEKFKG (SEQ ID NO: 69) | GGTGSFDY (SEQ ID NO: 46) |
| 20 | GYTFTIYPIS (SEQ ID NO: 32) | NFHPYLGDANYNEKFKG (SEQ ID NO: 70) | GGTGSFDY (SEQ ID NO: 46) |

TABLE 2 -continued

| Fab | HCDR1 | HCDR2 | HCDR3 |
|---|---|---|---|
| 21 | GYTFTIYPIS (SEQ ID NO: 32) | NFHPYLGDTNYNEKFKG (SEQ ID NO: 44) | GGFGSFDY (SEQ ID NO: 72) |
| 22 | GYTFTIYPIS (SEQ ID NO: 32) | NFHPYLGDTNYNEKFKG (SEQ ID NO: 44) | GGTGAFDY (SEQ ID NO: 73) |
| 23 | GYTFTIYPIS (SEQ ID NO: 32) | NFHPYLGDTNYNEKFKG (SEQ ID NO: 44) | GGTGSFPY (SEQ ID NO: 74) |
| *Consensus | GYTFX$_8$IYPI X$_9$ (SEQ ID NO: 65) | NFHPYLGX$_{10}$X$_{11}$NYNEKFKG (SEQ ID NO: 71) | GGX$_{12}$GX$_{13}$FX$_{14}$Y (SEQ ID NO: 75) |

*X$_8$ is T, W, Y, or L; X$_9$ is S or E; X$_{10}$ is D, T, L, V, or M; X$_{11}$ is T or A; X$_{12}$ is T or F; X$_{13}$ is S or A; X$_{14}$ is D or P

The SEQ ID NOs of the amino acid sequences and consensus amino acid sequences encoding more preferred CDRs for antibodies of the present invention are provided in Table 3 below.

TABLE 3

| Fab | LCDR1 SEQ ID NO: | LCDR2 SEQ ID NO: | LCDR3 SEQ ID NO: | HCDR1 SEQ ID NO: | HCDR2 SEQ ID NO: | HCDR3 SEQ ID NO: |
|---|---|---|---|---|---|---|
| 1.5 | 43 | 57 | 61 | 63 | 80 | 46 |
| 1.7 | 43 | 58 | 61 | 32 | 81 | 46 |
| 1.10 | 43 | 53 | 61 | 63 | 82 | 46 |
| 1.13 | 43 | 57 | 61 | 63 | 83 | 46 |
| 1.15 | 43 | 30 | 61 | 63 | 82 | 46 |
| 3.2 | 43 | 53 | 61 | 63 | 84 | 46 |
| 3.6 | 43 | 53 | 61 | 32 | 84 | 46 |
| 3.7 | 43 | 57 | 61 | 63 | 85 | 46 |
| 3.8 | 43 | 53 | 31 | 63 | 84 | 46 |
| 3.9 | 43 | 53 | 61 | 63 | 86 | 46 |
| 3.12 | 43 | 57 | 61 | 63 | 84 | 46 |
| 3.23 | 43 | 53 | 61 | 63 | 85 | 46 |
| Hu22 | 43 | 30 | 31 | 32 | 44 | 46 |
| L1.5 | 41 | 53 | 31 | 63 | 84 | 46 |
| H1.39 | 43 | 53 | 31 | 78 | 84 | 46 |
| *Consensus | 42 | 76 | 62 | 79 | 87 | 46 |

Human light chain constant regions are classified as kappa or lambda and characterized by a particular constant region as known in the art. Human heavy chain constant regions are classified as gamma, mu, alpha, delta, or epsilon, and define the antibody's isotype as IgG, IgM, IgA, IgD, and IgE, respectively and several of these may be further divided into subclasses e.g., IgG$_1$, IgG$_2$, IgG$_3$, IgG$_4$. Each heavy chain type has a particular constant region with a sequence readily known in the art. Light chain constant region kappa and heavy chain constant regions IgG$_1$, IgG$_2$, and IgG$_4$ are preferred constant regions in the antibodies of the invention. Preferred human heavy chain constant regions for the antibodies of the present invention are the heavy chain constant region amino acid sequences as shown in SEQ ID NOs: 90-94 and any variant thereof having 1, 2, 3, 4, 5, 6, 7, 8, 9, 10, 11, 12, 13, 14, or about 15 amino acid changes (including substitutions, insertions or deletions). More preferably, human heavy chain constant regions of the antibodies of the present invention are the heavy chain constant region amino acid sequences as shown in SEQ ID NOs: 93 and 94. Most preferably, the human heavy chain constant region of the antibodies of the present invention is the heavy chain constant region amino acid sequence shown in SEQ ID NO: 93. Preferred human light chain constant regions of the antibodies of the present invention are the light chain constant region kappa amino acid sequence shown in SEQ ID NO: 89 and any variant thereof having 1, 2, 3, 4, 5, 6, 7, 8, 9, or about 10 amino acid changes (including substitutions, insertions or deletions). Most preferably, the human light chain constant region of the antibodies of the present invention is the light chain constant region kappa amino acid sequence as shown in SEQ ID NO: 89.

As used herein, the "antigen-binding region" or "antigen-binding portion" refers to that portion of an antibody molecule, within the variable region, which contains the amino acid residues that interact with an antigen and confer on the antibody its specificity and affinity for the antigen. This antibody portion includes the framework amino acid residues necessary to maintain the proper conformation of the antigen-binding residues.

The present invention includes an antibody that selectively binds hepcidin-25 with a K$_D$ of about 800 pM or less as determined by SPR at 25° C. and wherein the antibody comprises at least one CDR selected from the group consisting of i) a HCDR3 having the amino acid sequence as shown in SEQ ID NO: 75, and ii) a LCDR3 having the amino acid sequence as shown in SEQ ID NO: 62. Preferably, such an antibody comprises six CDRs comprising amino acid and/or consensus amino acid sequences selected from the group consisting of: (i) LCDR1, LCDR2, LCDR3, HCDR1, HCDR2, and HCDR3 having the amino acid sequences as shown in SEQ ID NOs: 52, 60, 62, 65, 71, and 75, respectively; and (ii) LCDR1, LCDR2, LCDR3, HCDR1, HCDR2, and HCDR3 having the amino acid sequences as shown in SEQ ID NOs: 42, 76, 62, 79, 87, and 46, respectively. More preferably, an antibody of the present invention comprises six CDRs selected from the group consisting of: (i) LCDR1, LCDR2, LCDR3, HCDR1, HCDR2, and HCDR3 having the amino acid sequences as shown in SEQ ID NOs: 41, 53, 31, 63, 84, and 46, respectively; (ii) LCDR1, LCDR2, LCDR3, HCDR1, HCDR2, and HCDR3 having the amino acid sequences as shown in SEQ ID NOs: 43, 30, 31, 32, 44, and 46, respectively; (iii) LCDR1, LCDR2, LCDR3, HCDR1, HCDR2, and HCDR3 having the amino acid sequences as shown in SEQ ID NOs: 43, 53, 61, 63, 85, and 46, respectively; and (iv) LCDR1, LCDR2, LCDR3, HCDR1, HCDR2, and HCDR3 having the amino acid sequences as shown in SEQ ID NOs: 43, 57, 61, 63, 84, and 46, respectively. Even more preferably, the antibody of the invention comprises two heavy chain polypeptides and two light chain polypeptides, and wherein each of the heavy chain polypeptides have the amino acid sequence as shown in SEQ ID NO: 9 and each of the light chain polypeptides have the amino acid sequence as shown in SEQ ID NO: 17. Even more preferably, the antibody has an IC$_{50}$ between about 100 nM and about 50 nM in the hepcidin-induced ferroportin internalization assay described in Example 3, a k$_{off}$ rate from human hepcidin-25 between about between about $5.5 \times 10^{-4}$ s$^{-1}$ and about $2.0 \times 10^{-4}$ s$^{-1}$, as determined by SPR at 25° C., and selectively binds human hepcidin-25 with a $K_D$ between about 100 pM and about 50 pM. Most preferably, the antibody of the invention comprises two heavy chain polypeptides and two light chain polypeptides, and wherein each of the heavy chain polypeptides have the amino acid sequence as shown in SEQ ID NO: 8 and each of the light chain polypeptides have the amino acid sequence as shown in SEQ ID NO: 16, wherein the antibody has an $IC_{50}$ between about 100 nM and about 50 nM in the hepcidin-induced ferroportin internalization assay described in Example 3, a $k_{off}$ rate from human hepcidin-25 between about between about $5.5\times10^{-4}$ s$^{-1}$ and about $2.0\times10^{-4}$ s$^{-1}$, as determined by SPR at 25° C., and selectively binds human hepcidin-25 with a $K_D$ between about 100 pM and about 50 pM.

Other preferred antibodies of the invention comprise a LCVR having an amino acid sequence selected from the group consisting of SEQ ID NOs: 124, 125, 126, and 127. More preferably, an antibody of the invention comprises a HCVR having an amino acid sequence selected from the group consisting of SEQ ID NOs: 148, 128, 150, and 151. Even more preferably, an antibody of the invention comprises a LCVR of SEQ ID NO: 126 and a HCVR of SEQ ID NO: 148. Even more preferably, an antibody of the invention comprises a LCVR of SEQ ID NO: 127 and a HCVR of SEQ ID NO: 128. Even more preferably, an antibody of the invention comprises a LCVR of SEQ ID NO: 125 and a HCVR of SEQ ID NO: 151. A most preferred antibody of the invention comprises a LCVR of SEQ ID NO: 124 and a HCVR of SEQ ID NO: 150. Such LCVRs are preferably linked to a light chain constant region of human origin or derived from a light chain constant region of human origin, preferably a human kappa chain, and most preferably a kappa chain of SEQ ID NO: 89. Such HCVRs are preferably linked to a heavy chain constant region of human origin or derived from a heavy chain constant region of human origin, preferably $IgG_1$, $IgG_2$, or $IgG_4$, more preferably, a heavy chain constant region comprising an amino acid sequence selected from the group consisting of SEQ ID NOs: 90, 91, 92, 93, and 94, and most preferably, a heavy chain constant region comprising the amino acid sequence of SEQ ID NO: 93. Preferably, the antibody has an $IC_{50}$ between about 100 nM and about 50 nM in the hepcidin-induced ferroportin internalization assay described in Example 3, a $k_{off}$ rate from human hepcidin-25 between about between about $5.5\times10^{-4}$ s$^{-1}$ and about $2.0\times10^{-4}$ s$^{-1}$, as determined by SPR at 25° C., and selectively binds human hepcidin-25 with a $K_D$ between about 100 pM and about 50 pM.

An antibody of the invention may comprise a heavy chain polypeptide having an amino acid sequence as shown in SEQ ID NO: 6 and a light chain polypeptide having an amino acid sequence as shown in SEQ ID NO: 14. A heavy chain polypeptide having an amino acid sequence as shown in SEQ ID NO: 6 may be encoded by a polynucleotide sequence of SEQ ID NO: 2. A light chain polypeptide having an amino acid sequence as shown in SEQ ID NO: 14 may be encoded by a polynucleotide having the nucleic acid sequence as shown in SEQ ID NO: 10.

An antibody of the invention comprises a heavy chain polypeptide having an amino acid sequence as shown in SEQ ID NO: 7 and a light chain polypeptide having an amino acid sequence as shown in SEQ ID NO: 15. A heavy chain polypeptide having an amino acid sequence as shown in SEQ ID NO: 7 may be encoded by a polynucleotide sequence of SEQ ID NO: 3. A light chain polypeptide having an amino acid sequence as shown in SEQ ID NO: 15 may be encoded by a polynucleotide having the nucleic acid sequence as shown in SEQ ID NO: 11.

An antibody of the invention also comprises a heavy chain polypeptide having an amino acid sequence as shown in SEQ ID NO: 8 and a light chain polypeptide having an amino acid sequence as shown in SEQ ID NO: 16. A heavy chain polypeptide having an amino acid sequence as shown in SEQ ID NO: 8 may be encoded by a polynucleotide sequence as shown in SEQ ID NO: 4. A light chain polypeptide having an amino acid sequence as shown in SEQ ID NO: 16 may be encoded by a polynucleotide having the nucleic acid sequence as shown in SEQ ID NO: 12.

In another embodiment, an antibody of the invention comprises a heavy chain polypeptide having an amino acid sequence as shown in SEQ ID NO: 9 and a light chain polypeptide having an amino acid sequence as shown in SEQ ID NO: 17. A heavy chain polypeptide having an amino acid sequence as shown in SEQ ID NO: 9 may be encoded by a polynucleotide sequence of SEQ ID NO: 5. A light chain polypeptide having an amino acid sequence as shown in SEQ ID NO: 17 may be encoded by a polynucleotide having the nucleic acid sequence as shown in SEQ ID NO: 13.

Preferred human engineered antibodies of the invention are referred to herein as Mabs L1.5, Hu22, 3.12, and 3.23. The SEQ ID NOs of the amino acid sequences encoding the heavy chains, the light chains, the heavy and light chain variable regions, and the CDRs for Mabs L1.5, Hu22, 3.12, and 3.23 are provided in Table 4 below.

TABLE 4

| Mab | Heavy Chain | Light Chain | HCVR | HCCDR1 | HCCDR2 | HCCDR3 | LCVR | LCCDR1 | LCCDR2 | LCCDR3 |
| --- | --- | --- | --- | --- | --- | --- | --- | --- | --- | --- |
| L1.5 | 6 | 14 | 148 | 63 | 84 | 46 | 126 | 41 | 53 | 31 |
| Hu22 | 7 | 15 | 128 | 32 | 44 | 46 | 127 | 43 | 30 | 31 |
| 3.12 | 8 | 16 | 150 | 63 | 84 | 46 | 124 | 43 | 57 | 61 |
| 3.23 | 9 | 17 | 151 | 63 | 85 | 46 | 125 | 43 | 53 | 61 |

Standard molecular biology techniques are used to prepare the recombinant expression vector, transfect the host cells, select for transformants, isolated host cell lines producing an antibody of the invention, culture these host cells and recover the antibody from the culture medium.

The present invention is also directed to host cells that express an anti-hepcidin antibody of the invention. A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably-linked in one vector or, alternatively, the heavy chain and the light chain may be expressed independently from different promoters to which they are operably-linked in two vectors—one expressing the heavy chain and one expressing the light chain. Optionally, the heavy chain and light chain may be expressed in different host cells.

Additionally, the recombinant expression vector can encode a signal peptide that facilitates secretion of the antibody light and/or heavy chain from a host cell. The antibody light and/or heavy chain gene can be cloned into the vector such that the signal peptide is operably-linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR can be converted to a full-length heavy chain gene by operably-linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g., $IgG_1$, $IgG_2$, $IgG_3$ and $IgG_4$) or subclass constant region and any allotypic variant thereof as described in Kabat (supra).

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and/or polyoma virus.

Additionally, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vectors) encoding the heavy and/or light chains is introduced into a host cell by standard techniques e.g., electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies of the invention include Chinese Hamster Ovary (CHO cells) [including dhfr minus CHO cells, as described in Urlaub and Chasin, Proc. Natl. Acad. Sci. USA 77:4216-20, 1980, used with a DHFR selectable marker, e.g., as described in Kaufman and Sharp, J. Mol. Biol. 159:601-21, 1982], NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

Host cells can also be used to produce portions, or fragments, of intact antibodies, e.g., Fab fragments or scFv molecules by techniques that are conventional. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to human hepcidin-25. The molecules expressed from such truncated DNA molecules are also encompassed by the antibodies of the invention.

The invention provides a host cell comprising a nucleic acid molecule of the present invention. Preferably a host cell of the invention comprises one or more vectors or constructs comprising a nucleic acid molecule of the present invention. For example, a host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably-linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxylapatite chromatography, gel electrophoresis, and the like. Standard procedures for purification of therapeutic antibodies are described, for example, by Feng Li, Joe X. Zhou, Xiaoming Yang, Tim Tressel, and Brian Lee in an article entitled "Current Therapeutic Antibody Production and Process Optimization" (BioProcessing Journal, September/October 2005), for example. Additionally, standard techniques for removing viruses from recombinantly expressed antibody preparations are also known in the art (see, for example, Gerd Kern and Mani Krishnan, "Viral Removal by Filtration: Points to Consider" (Biopharm International, October 2006)). The effectiveness of filtration to remove viruses from preparations of therapeutic antibodies is known to be at least in part dependent on the concentration of protein and/or the antibody in the solution to be filtered. The purification process for antibodies of the present invention may include a step of filtering to remove viruses from the mainstream of one or more chromatography operations. Preferably, prior to filtering through a pharmaceutical grade nanofilter to remove viruses, a chromatography mainstream containing an antibody of the present invention is diluted or concentrated to give total protein and/or total antibody concentration of about 1 g/L to about 3 g/L. Even more preferably, the nanofilter is a DV20 nanofilter (e.g., Pall Corporation; East Hills, N.Y.). Substantially pure immunoglobulins of at least about 90%, about 92%, about 94% or about 96% homogeneity are preferred, and about 98 to about 99% or more homogeneity most preferred, for pharmaceutical uses. Once purified, partially or to homogeneity as desired, the sterile antibodies may then be used therapeutically, as directed herein.

In view of the aforementioned discussion, the present invention is further directed to an antibody obtainable by a process comprising the steps of culturing a host cell including, but not limited to a mammalian, plant, bacterial, transgenic animal, or transgenic plant cell which has been transformed by a polynucleotide or a vector comprising nucleic acid molecules encoding antibodies of the invention so that the nucleic acid is expressed and, optionally, recovering the antibody from the host cell culture medium. Preferably, the host cell comprises a vector comprising a nucleic acid molecule encoding a light chain polypeptide having the amino acid sequence as shown in SEQ ID NOs: 14, 15, 16, or 17. More preferably, the host cell comprises a vector comprising a nucleic acid molecule as shown in SEQ ID NO: 12 or 13. Even more preferably, the transformed host cell is a Chinese hamster ovary, NS0 myeloma, COS, or SP2/0 cell.

The present invention is further directed to a method of producing an antibody of the invention comprising the steps of transforming a host cell including, but not limited to a mammalian, plant, bacterial, transgenic animal, or transgenic plant cell with a polynucleotide or a vector comprising a nucleic acid molecule encoding an antibody of the invention so that the nucleic acid is expressed and recovering the antibody from the host cell culture medium. Preferably, the host cell is transformed with a vector comprising a nucleic acid molecule encoding a light chain polypeptide having the amino acid sequence as shown in SEQ ID NOs: 14, 15, 16, or 17. More preferably, the host cell has been transformed with a vector comprising a nucleic acid molecule as shown in SEQ ID NO: 12 or 13. Even more preferably, the host cell is a Chinese hamster ovary, NS0 myeloma, COS, or SP2/0 cell.

The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially purified from proteins or polypeptides or other contaminants that are found in its natural environment that would interfere with its use (therapeutic, diagnostic, prophylactic, research or otherwise).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, an antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present.

As used herein, "substantially pure" or "substantially purified" means a compound or species that is the predominant species present (i.e., on a molar basis it is more abundant than any other individual species in the composition). In certain embodiments, a substantially purified composition is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

The present invention further provides an isolated polynucleotide that encodes the amino acid sequence selected from the group consisting of SEQ ID NOs: 124, 125, 126, 127, 128, 148, 150, and 151.

In another embodiment, the present invention provides a recombinant expression vector comprising polynucleotide that encodes the amino acid sequence selected from the group consisting of SEQ ID NOs: 124, 125, 126, 127, 128, 148, 150, and 151.

The phrase "human engineered antibodies" as used herein refers to an antibody wherein at least one portion is of human origin. Furthermore, as used herein, the phrase "human engineered antibodies" refer to the specific antibodies disclosed herein as well as additional antibodies that have similar functional properties according to the invention as the antibodies disclosed herein and have framework regions that are substantially human or fully human surrounding CDRs that are derived from a non-human antibody. Substantially human frameworks are those that have at least 80% sequence identity to a known human germline framework sequence. Preferably, the substantially human frameworks have at least about 85%, about 90%, about 95%, or about 99% sequence identity to a known human germline framework sequence. Most preferably, human engineered antibodies of the present invention contain minimal sequence derived from a non-human antibody.

For example, the human engineered antibody can comprise portions derived from an antibody of nonhuman origin, such as a mouse, and portions derived from an antibody of human origin, joined together, e.g., chemically by conventional techniques (e.g., synthetic) or prepared as a contiguous polypeptide using genetic engineering techniques. As used herein, the term "framework" when used in reference to an antibody variable region is entered to mean all amino acid residues outside the CDRs within the variable region of an antibody. As used herein, the term "framework region" is intended to mean each domain of the framework that is separated by the CDRs. The framework regions for the light chain are similarly separated by each of the light chain variable region CDRs. Preferably, the light chain variable region and/or heavy chain variable region comprises a framework or at least a portion of a framework region (e.g., containing 2 or 3 subregions, such as FR2 and FR3). More preferably, at least FRL1, FRL2, FRL3, or FRL4 is fully human or at least FRH1, FRH2, FRH3, or FRH4 is fully human. Even more preferably, at least FRL1, FRL2, FRL3, or FRL4 is a germline sequence (e.g., human germline) or comprises human consensus sequences for the particular framework known in the art and/or at least FRH1, FRH2, FRH3, or FRH4 is a germline sequence (e.g., human germline) or comprises human consensus sequences for the particular framework. In preferred embodiments, an antibody of the present invention comprises human germline light chain framework sequences and human germline heavy chain framework sequences (see, e.g., PCT WO 2005/005604). More preferably, human germline light chain frameworks are selected from the group consisting of: A11, A17, A18, A19, A20, A27, A30, L1, L11, L12, L2, L5, L6, L8, O12, O18, O2, and O8. Even more preferably, the human germline light chain framework is O2 or O18. Most preferably, the human germline light chain framework is O2. Additionally, preferred human germline heavy chain frameworks are selected from the group consisting of: VH2-5, VH2-26, VH2-70, VH3-20, VH3-72, VH1-24, VH1-46, VH3-9, VH3-66, VH3-74, VH4-31, VH1-18, VH1-69, VH3-7, VH3-11, VH3-15, VH3-21, VH3-23, VH3-30, VH3-48, VH4-39, VH4-59, VH5-51, VH3-73, VH1-58, VH1-3, and VH1-2. Even more preferably, the human germline heavy chain framework is VH1-69 or VH1-18. Most preferably, the human germline heavy chain framework is VH1-69

Human engineered antibodies in addition to those disclosed herein that selectively bind human hepcidin-25 with the functional properties according to the invention can be generated using several different approaches. The specific antibodies disclosed herein can be used as a template or parent antibody to make additional antibodies. In one approach the parent antibody CDRs are grafted into a human framework that has a high sequence identity with the parent antibody framework. The sequence identity of the new framework will generally be at least 80%, at least 85%, or at least 90% with the corresponding framework in the parent antibody. This grafting may result in a reduction in binding affinity compared to the parent antibody. If this is the case, the framework can be back-mutated to the parent framework at certain positions based on specific criteria published by Queen et al. The identification of residues to consider for back-mutation may be carried out as follows: When an amino acid falls under the following category, the framework amino acid of the human germ-line sequence that is being used (acceptor framework) is replaced by a framework amino acid from a framework of the parent antibody (donor framework):

(a) the amino acid in the human framework of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model [Queen, et al., *Proc. Natl. Acad. Sci. USA* 88, 2869 (1991)].

When each of the amino acids in the human framework of the acceptor framework and a corresponding amino acid in the donor framework is unusual generally for human frameworks at that position, such an amino acid may be replaced by an amino acid typical for human frameworks at that position. This back-mutation criteria enables one to recover the activity of the parent.

Another approach would be to randomly mutate the grafted CDRs without changing the framework and screen such antibodies for binding affinity that is as good or better than the parent antibody. Further, a combination of both these approaches is possible. After grafting, specific framework regions may be back-mutated in addition to making changes in the CDRs. This general methodology is described by Wu, et al., (1999), "Humanization of a murine monoclonal antibody by simultaneous optimization of framework and CDR residues", J. Mol. Biol., 294:151-162.

As used herein, the term "donor" is intended to mean a parent antibody molecule or fragment thereof from which a portion is derived from, given or contributes to another antibody molecule or fragment thereof so as to confer either a structural or functional characteristic of the parent molecule onto the receiving molecule. For the specific example of CDR grafting, the parent molecule from which the grafted CDRs are derived is a donor molecule. The donor CDRs confer binding affinity of the parent molecule onto the receiving molecule. It should be understood that a donor molecule does not have to be from a different species as the receiving molecule of fragment thereof. Instead, it is sufficient that the donor is a separate and distinct molecule.

As used herein, the term "acceptor" is intended to mean an antibody molecule or fragment thereof which is to receive the donated portion from the parent or donor antibody molecule or fragment thereof. An acceptor antibody molecule or fragment thereof is therefore imparted with the structural or functional characteristic of the donated portion of the parent molecule. For the specific example of CDR grafting, the receiving molecule for which the CDRs are grafted is an acceptor molecule. The acceptor antibody molecule or fragment is imparted with the binding affinity of the donor CDRs or parent molecule. As with a donor molecule, it is understood that an acceptor molecule does not have to be from a different species as the donor.

A "variable region" when used in reference to an antibody or a heavy or light chain thereof is intended to mean the amino terminal portion of an antibody which confers antigen binding onto the molecule and which is not the constant region.

The term is intended to include functional fragments thereof which maintain some of all of the binding function of the whole variable region. Therefore, the term "heteromeric variable region binding fragments" is intended to mean at least one heavy chain variable region and at least one light chain variable regions or functional fragments thereof assembled into a heteromeric complex. Heteromeric variable region binding fragments include, for example, functional fragments such as Fab, F(ab)2, Fv, single chain Fv (scFv) and the like. Such functional fragments are well known to those skilled in the art. Accordingly, the use of these terms in describing functional fragments of a heteromeric variable region is intended to correspond to the definitions well known to those skilled in the art. Such terms are described in, for example, Harlow and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Plvckthun and Skerra, Meth. Enzymol., 178:497-515 (1989) and in Day, E. D., Advanced Immunochemistry, Second Ed., Wiley-Liss, Inc., New York, N.Y. (1990).

Preferably, a human engineered antibody has CDRs that originate from or are derived from a parent antibody, i.e., a non-human antibody, preferably a mouse antibody or fragment thereof such as the mouse Fab JXB7, while framework and constant region, to the extent it is present, (or a significant or substantial portion thereof, i.e., at least about 90%, 92%, 94%, 95%, 96%, 97%, 98% or 99%) are encoded by nucleic acid sequence information that occurs in the human germline immunoglobulin region (see, e.g., the International ImMuno-GeneTics Database) or in recombined or mutated forms thereof whether or not said antibodies are produced in a human cell. Preferably, at least two, three, four, five or six CDRs of a human engineered antibody are optimized from the CDRs of a non-human parent antibody from which the human engineered antibody was derived, to generate a desired property, e.g., improved specificity, affinity or neutralization, which may be identified by a screening assay, e.g., an ELISA assay. Preferably, an antibody of the invention comprises a HCDR3 identical to the HCDR3 of the parent mouse Fab JXB7 (i.e., SEQ ID NO: 46) and HCDR1, HCDR2, LCDR1, LCDR2, and LCDR3 comprise at least one amino acid substitution when compared to that present in the parent mouse Fab JXB7. Certain amino acid substitutions in the CDRs of human engineered antibodies of the invention as compared to those of the parent mouse Fab JXB7 decrease the likelihood of instability of the antibody (e.g., removal of one or more CDR Asn residues) or decrease the likelihood of immunogenicity of the antibody when administered to a human subject (e.g., as predicted by IMMUNOFILTER™ Technology (Xencor, Inc., Monrovia, Calif.)).

Human engineered antibodies may be subjected to in vitro mutagenesis using methods of routine use in the art and, thus, the framework region amino acid sequences of the HCVRs and LCVRs of the human engineered recombinant antibodies are sequences that, while derived from those related to human germline HCVR and LCVR sequences, may not naturally exist within the human antibody germline repertoire in vivo. It is contemplated that such amino acid sequences of the HCVR and LCVR frameworks of the human engineered recombinant antibodies are at least about 85%, about 90%, about 92%, about 94%, about 95%, about 96%, about 98% or, more preferably, at least about 99% or, most preferably, 100% identical to a human germline sequence. Accordingly, human engineered antibodies may comprise residues which are found neither in the recipient antibody nor in the CDR or framework sequences imported from the parent antibody.

There are multiple methods available in the art to generate human engineered antibodies (see, e.g., PCT International Patent Application Publication No. WO2006/06046935; Queen, et al., Proc. Natl. Acad. Sci. USA 88:2869 (1991); Jones et al., Nature, 321:522 (1986); Riechmann et al., Nature, 332:323-327 (1988); and Verhoeyen et al., Science, 239:1534 (1988)). For example, human engineered antibodies may be produced by obtaining nucleic acid sequences encoding the HCVR and LCVR of a parent antibody (e.g., a murine antibody or antibody made by a hybridoma) which selectively binds hepcidin-25, identifying the CDRs in said HCVR and LCVR (nonhuman), and grafting such CDR-encoding nucleic acid sequences onto selected human framework-encoding nucleic acid sequences. Optionally, a CDR region may be optimized by mutagenizing randomly or at particular locations in order to substitute one or more amino acids in the CDR with a different amino acid prior to grafting the CDR region into the framework. Alternatively, a CDR region may be optimized subsequent to insertion into the human framework using methods available to one of skill in the art.

After the CDR-encoding sequences are grafted onto the selected human framework encoding sequences, the resultant DNA sequences encoding the human engineered variable heavy and variable light sequences are then expressed to produce a human engineered antibody that selectively binds hepcidin-25. The human engineered HCVR and LCVR may be expressed as part of a whole anti-hepcidin-25 antibody molecule, i.e., as a fusion protein with human constant domain sequences. However, the HCVR and LCVR sequences can also be expressed in the absence of constant sequences to produce a human engineered anti-hepcidin-25 selective Fv or Fab, for example (see, e.g., Watkins, J., et al., Anal. Biochem., 253:37-45 (1997) and Watkins, J., et al., Anal. Biochem. 256:169-177, (1998)).

It will be appreciated that applying the teaching of the present invention the person skilled in the art may use common techniques e.g. site directed mutagenesis, to substitute, add, or delete amino acids within the specific CDR and framework sequences herein disclosed and in so doing generate further variable region amino acid sequences derived from the sequences herein provided. Up to all 21 alternative naturally occurring amino acids may be introduced at a specific substitution site. Finally, in vitro or in vivo screening technologies such as those described in Example 2 herein are available to the artisan for the selection of variable region amino acid sequences for Fab fragments having the desired binding affinity to hepcidin polypeptides. In this way further Fab fragments may be identified that are suitable for preparing an anti-hepcidin antibody in accordance with the present invention. Preferably, amino acid substitution, addition, and deletion within the frameworks is restricted to one, two, three, or four positions within one or each of the framework region sequences (i.e., FRL1, FRL2, FRL3, FRL4, FRH1, FRH2, FRH3, FRH4) disclosed herein. Preferably, amino acid substitution, addition, and deletion within the CDRs is restricted to one to three positions within one or each CDR, more preferably substitution, addition, and deletion at one or two amino acid positions within one or each CDR is performed. Further preferred, amino acid substitution, addition, and deletion is performed at one or two amino acid positions in the CDRs of the heavy chain variable region. Most preferably amino acid substitution, addition, and deletion is performed at one or two amino acid positions within CDRH2.

The resultant DNA sequences encoding the human engineered variable heavy and variable light sequences are then expressed to produce a human engineered antibody that selectively binds human hepcidin-25 with high affinity. The human engineered HCVR and LCVR may be expressed as part of a whole anti-hepcidin-25 antibody molecule, i.e., as a fusion protein with human constant domain sequences.

Another aspect of the invention provides methods of using the antibodies of the invention in relatively simple yet highly sensitive and selective immunoassays for the detection and measurement of mature hepcidin in human tissues and biological fluids for diagnostic and prognostic purposes.

The antibodies of the present invention provide the means to accurately detect or determine the amounts of mature hepcidin in a tissue or biological fluid from a human for assessment of predispositions to mature hepcidin-promoted disorders, and for detection and diagnosis of such disorders in patients suffering therefrom. For example, the antibodies of the invention can be incorporated into sensitive and reliable immunoassays such as ELISA, RIA, immunodiffusion assays, or immuno-detection assays, such as SPR assays. Similarly, the antibodies of the present invention are also useful for immunohistochemical (IHC) and immunofluorescence (IF) assays of tissue or biological fluid samples. Such analyses can be used to detect aberrant levels of hepcidin-25 and hence to diagnose hepcidin-25 promoted disorders. More specifically, the present invention provides methods of diagnosing a human mature hepcidin-promoted disorder in a patient by determining the level of human mature hepcidin in a sample of tissue or a biological fluid from the patient and comparing the level of human mature hepcidin in the sample with the level of human mature hepcidin in a corresponding sample from one or more control individuals or with a reference standard thereby detecting a disorder associated with elevated levels of human mature hepcidin. The disease state may comprise one or more of a genetic or non-genetic disease associated with decreased serum iron levels, reticulocyte count, red blood cell count, hemoglobin, and/or hematocrit. Preferably the disease state may comprise one or more of a disorder associated with anemia.

A method of monitoring a human mature hepcidin-promoted disease, disorder or condition in a patient is also provided. The method includes determining the level of human mature hepcidin in a sample of a tissue or biological fluid from a patient suffering from, or at risk of, a human mature hepcidin-promoted disease, disorder or condition at a first time point; determining the level of human mature hepcidin in one or more samples of tissue or biological fluid from the patient at one or more different time points; comparing the levels of human mature hepcidin determined at different time points and thereby monitoring the human mature hepcidin-promoted disease or condition.

The human mature hepcidin selective antibodies of the present invention are particularly useful when applied to high-throughput methods. Such methods include micro-chip and micro-array methods, such that many samples can be tested on a microplate or slide, or other assay substrate known in the art.

The presence of human mature hepcidin or levels thereof in a biological sample may be established by combining the biological sample with, e.g., an antibody of the invention under conditions suitable to form an antigen-antibody complex. The antibody is directly or, more preferably, indirectly labeled with a detectable moiety to facilitate detection of the bound or unbound antibody. A wide variety of methods of detection of immunocomplex formation are well known in the art, for example, ELISA, RIA, immunoblot (e.g., dot blot, slot blot, western blot, etc.), indirect immunofluorescence techniques and methods that rely on detection of changes in physical parameters, such as for instance, SPR, and the like. Such applications include methods that utilize a hepcidin-25 selective antibody of the invention conjugated with a detectable moiety to detect hepcidin in a biological sample, e.g., in a human biological fluid or in a cell or tissue extract. Antibodies of the invention may be used in such assays with or without modification with a detectable moiety. If modified with a detectable moiety, antibodies of the invention may be modified by covalent or non-covalent attachment of the detectable moiety. As used herein, the term "detectable" describes a feature of a substance (a conjugate, compound, or moiety) that allows identifying or tracing the substance by a detector, using known analytical techniques. Representative examples of detectable moieties include, without limitation, chromophores, fluorescent moieties, phosphorescent moieties, luminescent moieties, radioactive moieties, various enzymes (such as alkaline phosphatase, or horseradish peroxidase), magnetic moieties (e.g., diamagnetic, paramagnetic and ferromagnetic materials), and heavy metal clusters, as well as any other known detectable moieties. The amount of an antibody-antigen standard complex formed may be quantitated by various methods known in the art, such as, e.g., photometric or colorimetric means. Preferably, the antibodies of the invention are used without modification, i.e., indirectly labeled, according to methods well known in the art.

The invention embodies a method for detecting human mature hepcidin protein in a biological sample, comprising incubating an antibody of the invention with a biological sample under conditions and for a time sufficient to permit said antibody to bind to human mature hepcidin proteins, and detecting said binding.

The present invention also provides compositions, methods and kits for screening samples suspected of containing human mature hepcidin polypeptides. Such screening may be performed on patient samples, or laboratory samples suspected of containing or producing such polypeptide. A kit can contain a hepcidin-25 selective antibody of the present invention. The kit can contain a suitable buffer and reagents for detecting an interaction between a sample and a hepcidin-25 selective antibody of the present invention. The provided reagent can be radiolabeled, fluorescently-labeled or enzymatically-labeled agent capable of binding or interacting with an antibody of the present invention such as an anti-mouse IgG antibody.

The reagent of the kit can be provided as a liquid solution, attached to a solid support or as a dried powder. When the reagent is provided in a liquid solution, preferably, the liquid solution is an aqueous solution. Preferably, when the reagent provided is attached to a solid support, the solid support can be chromatographic media, a test plate having a plurality of wells, or a microscope slide. When the reagent provided is a dry powder, the powder can be reconstituted by the addition of a suitable solvent, which may be provided in the kit as well.

The kit of the invention is provided in a container that generally includes a vial into which the antibody, antigen or detection reagent may be placed, and preferably suitably aliquotted. The kits of the present invention will also typically include a means for containing the antibody, antigen, and reagent containers for commercial sale. Such containers may include plastic containers into which the desired vials are retained and one or more necessary chemicals, such as chromatography material, solvents and eluents, test tubes, detergents, antibodies and chemicals for the detection reaction.

An antibody of the invention may be used to diagnose a disorder or disease associated with the activity of mature hepcidin. In a similar manner, the antibody of the invention can be used in an assay to monitor levels of mature hepcidin in a subject being treated for a condition, disease, or disorder promoted mature hepcidin. Such applications include methods that utilize an antibody of the invention and a label to detect mature hepcidin in a biological sample, e.g., in a human body fluid or in a cell or tissue extract. Antibodies of the invention may be used with or without modification, and may be labeled by covalent or non-covalent attachment of a detectable moiety.

A variety of conventional protocols for measuring protein levels in a biological sample, including e.g., ELISAs, RIAs, and FACS, are known in the art and provide a basis for diagnosing altered or abnormal levels of mature hepcidin expression. Normal or standard hepcidin levels present in a sample are established using any known technique, e.g., by combining a sample comprising a mature hepcidin polypeptide with, e.g., an antibody of the invention under conditions suitable to form an antigen:antibody complex. The antibody is directly or indirectly labeled with a detectable substance to facilitate detection of the bound or unbound antibody. Suitable detectable substances include various enzymes, prosthetic groups, fluorescent materials, luminescent materials and radioactive materials. The amount of a standard complex formed is quantitated by various methods, such as, e.g., photometric means. Amounts of mature hepcidin polypeptide present in samples are then compared with the standard values. A preferred antibody for use in diagnostic, prognostic, and/or monitoring assays, kits, and methods has (i) a heavy chain polypeptide having an amino acid sequence as shown in SEQ ID NO: NO: 6 and a light chain polypeptide having an amino acid sequence as shown in SEQ ID NO: 14; (ii) a heavy chain polypeptide having an amino acid sequence as shown in SEQ ID NO: 7 and a light chain polypeptide having an amino acid sequence as shown in SEQ ID NO: 15; (iii) a heavy chain polypeptide having an amino acid sequence as shown in SEQ ID NO: 9 and a light chain polypeptide has the amino acid sequence as shown in SEQ ID NO: 17; or (iv) a heavy chain polypeptide having an amino acid sequence as shown in SEQ ID NO: 8 and a light chain polypeptide has the amino acid sequence as shown in SEQ ID NO: 16.

An isolated hepcidin-25 selective antibody of the invention may be used in therapy, preferably, human therapy.

A pharmaceutical composition comprising an antibody of the invention may be used to increase serum iron levels, reticulocyte count, red blood cell count, hemoglobin, and/or hematocrit in a human when an effective amount is administered to a human subject in need thereof. Furthermore, an antibody of the invention may be useful for the treatment of conditions, diseases, or disorders wherein the presence of hepcidin-25 causes or contributes to undesirable pathological effects or a decrease of hepcidin-25 levels or hepcidin-25 bioactivity has a therapeutic benefit in human subjects. Such conditions, diseases or disorders include, but are not limited to, anemia including, but not limited to, anemia resulting from infection, inflammation, chronic disease, and/or cancer. Subjects may be male or female.

The present invention includes a method of increasing serum iron levels, reticulocyte count, red blood cell count, hemoglobin, and/or hematocrit that comprises administering to a human subject in need thereof, an effective amount of an antibody of the present invention that selectively binds human hepcidin-25 with a $K_D$ of about 800 µM or less. Additionally, or alternatively, the present invention includes a method for treating a disease, condition or disorder, in a human subject, which benefits from an increase in serum iron levels, reticulocyte count, red blood cell count, hemoglobin, and/or hematocrit, including, but not limited to, anemia, e.g., anemia resulting from infection, inflammation, chronic disease, and/or cancer. Preferably, the subject has or is at risk of having undesirably low serum iron level, low reticulocyte count, red blood cell count, hemoglobin, and/or hematocrit. More preferably, the subject is at risk for, or suffering from, anemia including, but not limited to, anemia resulting from infection, inflammation, chronic disease, and/or cancer. Even more preferably, the antibody comprises a LCVR comprising;

i) a LCDR1 having an amino acid sequence selected from the group consisting of SEQ ID NOs: 41 and 43;
ii) a LCDR2 having an amino acid sequence selected from the group consisting of SEQ ID NOs: 30, 53, 56, 57, 58, and 76; and
iii) a LCDR3 having an amino acid sequence selected from the group consisting of SEQ ID NOs: 31, 61, and 60; and a HCVR comprising;
i) a HCDR1 having an amino acid sequence selected from the group consisting of SEQ ID NOs: 32, 63, 78, and 79;
ii) a HCDR2 having an amino acid sequence selected from the group consisting of SEQ ID NOs: 44, 80, 81, 82, 83, 84, 85, 86, and 87; and
iii) a HCDR3 having an amino acid sequence as shown in SEQ ID NO: 46. Even more preferably, the antibody comprises a heavy chain and a light chain polypeptide having (i) the amino acid sequences as shown in SEQ ID NOs: 6 and 14, respectively; (ii) the amino acid sequences as shown in SEQ ID NOs: 7 and 15, respectively; (iii) the amino acid sequences as shown in SEQ ID NOs: 9 and 17, respectively; or (iv) amino acid sequences as shown in SEQ ID NOs: 8 and 16, respectively. Most preferably, the antibody comprises a heavy chain and a light chain polypeptide having the amino acid sequences as shown in SEQ ID NOs: 8 and 16, respectively.

Additionally, the use of an antibody of the invention for the preparation of a medicament for the treatment of anemia or at least one of the aforementioned disorders is contemplated. Preferably, the antibody comprises a LCVR comprising;

i) a LCDR1 having an amino acid sequence selected from the group consisting of SEQ ID NOs: 41 and 43;
ii) a LCDR2 having an amino acid sequence selected from the group consisting of SEQ ID NOs: 30, 53, 56, 57, 58, and 76; and
iii) a LCDR3 having an amino acid sequence selected from the group consisting of SEQ ID NOs: 31, 61, and 60; and a HCVR comprising;
i) a HCDR1 having an amino acid sequence selected from the group consisting of SEQ ID NOs: 32, 63, 78, and 79;
ii) a HCDR2 having an amino acid sequence selected from the group consisting of SEQ ID NOs: 44, 80, 81, 82, 83, 84, 85, 86, and 87; and
iii) a HCDR3 having an amino acid sequence as shown in SEQ ID NO: 46. More preferably, the antibody comprises a heavy chain and a light chain polypeptide having (i) the amino acid sequences as shown in SEQ ID NOs: 6 and 14, respectively; (ii) the amino acid sequences as shown in SEQ ID NOs: 7 and 15, respectively; (iii) the amino acid sequences as shown in SEQ ID NOs: 9 and 17, respectively; or (iv) amino acid sequences as shown in SEQ ID NOs: 8 and 16, respectively. Most preferably, the antibody comprises a heavy chain and a light chain polypeptide having the amino acid sequences as shown in SEQ ID NOs: 8 and 16, respectively.

The term "treating" (or "treatment" and "treat" are intended to refer to all processes wherein there may be a slowing, interrupting, arresting, controlling, or stopping of the progression of the disorders described herein, but does not necessarily indicate a total elimination of all disorder symptoms. "Treatment", as used herein, includes administration of a compound of the present invention for treatment of a disease or condition in a mammal, particularly in a human, and includes: (a) inhibiting further progression of the disease, i.e., arresting its development; and (b) relieving the disease, i.e., causing regression of the disease or disorder or alleviating symptoms or complications thereof. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation.

The term "preventing" (or "prevent" or "prevention") means prohibiting, restraining, or inhibiting the incidence or occurrence of a symptom, disorder, condition, or disease. Acute events and chronic conditions may be treated and prevented. In an acute event, an antibody of the invention is administered at the onset of a symptom, disorder, condition, or disease, and is discontinued when the acute event ends. In contrast, a chronic symptom, disorder, condition, or disease is treated over a more protracted time frame.

A "disorder" is any condition that would benefit from treatment according to the present invention. The terms "disorder", "condition" and "disease" are used interchangeably herein and include chronic and acute mature hepcidin-promoted disorders, including, but not limited to, anemia including, but not limited to, anemia of chronic disease, including, but not limited to, anemia resulting from infection, inflammation, and/or cancer.

An antibody of the invention can be incorporated into a pharmaceutical composition suitable for administration to a human subject. An antibody of the invention may be administered to a human subject alone or in combination with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents including but not limited to sodium chloride, stabilizing agents and the like are used as appropriate. Said compositions can be designed in accordance with conventional techniques disclosed in, e.g., *Remington, The Science and Practice of Pharmacy*, 19$^{th}$ Edition, Gennaro, Ed., Mack Publishing Co., Easton, Pa. 1995 which provides a compendium of formulation techniques as are generally known to practitioners. Suitable carriers for pharmaceutical compositions include any material which, when combined with an antibody of the invention, retains the molecule's activity and is non-reactive with the subject's immune system. In certain embodiments, a pharmaceutical composition of the present invention comprises i) an antibody of the invention, ii) a citrate buffer, and iii) sodium chloride. Preferably, the antibody is present at a concentration ranging from about 1 mg/ml to about 35 mg/ml, citrate is present at a concentration ranging from about 5 mM to about 20 mM, sodium chloride is present at a concentration ranging from about 100 mM to about 300 mM, and the pH of the composition is between about 5.0 to about 7.2. More preferably, the antibody is present at a concentration ranging from about 5 mg/ml to about 30 mg/ml, citrate is present at a concentration ranging from about 5 mM to about 15 mM, sodium chloride is present at a concentration ranging from about 150 mM to about 300 mM, and the pH of the composition is between about 5.5 to about 6.5. Even more preferably, the antibody is present at a concentration ranging from about 5 mg/ml to about 25 mg/ml, citrate is present at about 10 mM, sodium chloride is present at a concentration ranging from about 200 mM to about 300 mM, and the pH of the composition is between about 5.5 to about 6.5.

A pharmaceutical composition comprising an anti-hepcidin-25 antibody of the present invention can be administered to a subject at risk for or exhibiting pathologies as described herein, e.g., anemia disorders, using standard administration techniques.

The phrase "effective amount" as used herein refers to an amount necessary (at dosages and for periods of time and for the means of administration) to achieve the desired therapeutic result. An effective amount of the antibody may vary according to factors such as the disease state, age, gender, and weight of the individual, and the ability of the antibody or antibody portion to elicit a desired response in the individual. An effective amount is also one in which any toxic or detrimental effect of the antibody, are outweighed by the therapeutically beneficial effects.

An effective amount is at least the minimal amount, but less than a toxic amount, of an active agent which is necessary to impart therapeutic benefit to a subject. Stated another way, an effective amount or therapeutically effective amount of an antibody of the invention is an amount which in mammals, preferably humans, (i) increases serum iron levels, reticulocyte count, red blood cell count, hemoglobin, and/or hematocrit, or (ii) treats a disorder wherein the presence of mature hepcidin causes or contributes to an undesirable pathological effect, or (iii) a decrease in mature hepcidin levels or mature hepcidin bioactivity results in a beneficial therapeutic effect in a mammal, preferably a human, including, but not limited to, anemia including, but not limited to, anemia of chronic disease, including, but not limited to, anemia resulting from infection, inflammation, and/or cancer. An effective amount of an antibody of the invention may be administered in a single dose or in multiple doses. Furthermore, an effective amount of an antibody of the invention may be administered in multiple doses of amounts that would be less than an effective amount if not administered more than once.

As is well known in the medical arts, dosages for any one subject depends upon many factors, including the patient's size, body surface area, age, the particular compound to be administered, gender, time and route of administration, general health, and other drugs being administered concurrently. Dose may further vary depending on the type and severity of the disease. A typical dose can be, for example, in the range of about 1 mg to about 200 mg; preferably, about 2 mg to about 200 mg; more preferably, about 5 mg to about 200 mg; even more preferably, about 5 mg to about 50 mg, even more preferably, about 5 mg to about 25 mg; even more preferably, about 5 mg to about 20 mg; even more preferably, about 5 mg to about 15 mg; however, doses below or above this exemplary range are envisioned, especially considering the aforementioned factors. A daily parenteral dosage regimen can be from about 10 µg/kg to about 20 mg/kg, preferably from about 25 µg/kg to about 20 mg/kg, more preferably from about 50 µg/kg to about 20 mg/kg, even more preferably, from about 100 µg/kg to about 20 mg/kg, even more preferably from about 200 µg/kg to about 20 mg/kg, even more preferably, from about 300 µg/kg to about 20 mg/kg, even more preferably, from about 400 µg/kg to about 20 mg/kg, even more preferably from about 500 µg/kg to about 20 mg/kg, from about 600 µg/kg to about 20 mg/kg, from about 700 µg/kg to about 20 mg/kg, from about 800 µg/kg to about 20 mg/kg, from about 900 µg/kg to about 20 mg/kg, even more preferably, from about 1 mg/kg to about 20 mg/kg, even more preferably, from about 2 mg/kg to about 20 mg/kg, even more preferably, from about 3 mg/kg to about 20 mg/kg, even more preferably, from about 4 mg/kg to about 20 mg/kg, even more preferably, from about 5 mg/kg to about 20 mg/kg, even more preferably, from about 6 mg/kg to about 20 mg/kg, even more preferably, from about 7 mg/kg to about 20 mg/kg, and even more preferably, from about 8 mg/kg to about 20 mg/kg. Progress may be monitored by periodic assessment, and the dose adjusted accordingly.

These suggested amounts of antibody are subject to a great deal of therapeutic discretion. The key factor in selecting an appropriate dose and scheduling is the result obtained. Factors for consideration in this context include the particular disorder being treated, the clinical condition of the individual patient, the cause of the disorder, the site of delivery of the antibody, the particular type of antibody, the method of administration, the scheduling of administration, and other factors known to medical practitioners.

The route of administration of an antibody of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Parenteral delivery by intravenous or intraperitoneal or subcutaneous injection is preferred. Subcutaneous injection is most preferred. Suitable vehicles for such injections are well known in the art.

The pharmaceutical composition typically must be sterile and stable under the conditions of manufacture and storage in the container provided, including e.g., a sealed vial, syringe or other delivery device, e.g., a pen. Therefore, pharmaceutical compositions may be sterile filtered after making the formulation, or otherwise made microbiologically acceptable.

The following examples are offered for illustrative purposes only, and are not intended to limit the scope of the present invention.

EXAMPLES

Example 1

Production of Human Hepcidin-25

Human hepcidin-25 can be obtained from commercial sources (e.g., Peptide International (Louisville, Ky.)) or produced by a variety of synthetic or recombinant techniques known in the art. Alternatively, a fusion protein comprising the twenty-five amino acids of human hepcidin-25 sequence and having the amino acid sequence as shown in SEQ ID NO: 95 is expressed in E. coli. Inclusion bodies are isolated from 3 liters of E. coli expressing the human hepcidin fusion protein after a 3-6 hour induction with 1 mM IPTG at 37° C. The inclusion bodies are solubilized in buffer A (50 mM Tris and 8 M urea (pH 8.0)). The supernatant is passed over an IMAC column (20 mL resin). The column is washed with buffer A until the absorbance returned to baseline and the bound polypeptides are batch eluted from the column by 0.5 M imidazole in buffer A. The human hepcidin-25 fusion protein is pooled and reduced with 50 mM DTT. This fusion protein is then refolded by diluting pooled material into 2 M urea, 3 mM cysteine, 50 mM Tris (pH 8.0) to a final protein concentration less than 50 µg/mL. This material is stirred at room temperature and air oxidized for 48 hours. The oxidized polypeptides are passed over an IMAC column (20 mL) at a flow rate of 5 mL/min, and the human hepcidin-25 fusion protein is batch eluted from the column by 0.5 M imidazol in buffer A. The pooled fractions containing the human hepcidin-25 fusion protein are concentrated and passed over a Superdex 75 (GE Healthcare, XK26/60) sizing column equilibrated with 50 mM Tris, 4 M urea, pH 8.0, at a flow rate of 3 mL/min. The monomeric fusion protein is pooled and then diluted to 50 mM Tris, 2M urea, 5 mM $CaCl_2$, pH 8.0 and then is cleaved with enterokinase to produce human hepcidin-25 of SEQ ID NO: 1. Uncleaved human hepcidin-25 fusion protein is removed by passive IMAC chromatography (as outlined above). The flow through from the IMAC column is then passed over a C-18 Reversed Phase column at a flow rate of 4.0 mL/minute. The column is washed with 0.1% TFA in water until the absorbance returned to baseline and the bound polypeptides are eluted from the column with a linear gradient of ACN from 20% to 40% with 0.1% TFA at a rate of 0.5%/min. Fractions which contain the human hepcidin-25 polypeptide are pooled and analyzed by N-terminal amino acid sequencing and matrix assisted laser desorption/ionization mass spectrometry (MALDI-MS). Polypeptides encoding rat, mouse, and cynomolgous monkey hepcidin-25 and various N-terminally truncated forms of human hepcidin-25, including hepcidin-22 and hepcidin-20 were obtained commercially (e.g., Peptide International).

Example 2

Affinity Binding Measurements of Anti-Hepcidin-25 Fabs and Mabs

A surface plasmon resonance biosensor such as the BIAcore® T100 may be used to measure binding kinetics and affinity of the antibodies disclosed herein. The BIAcore® system utilizes the optical properties of SPR to detect alteration in protein concentration of interacting molecules within a dextran biosensor matrix. Except as noted, all reagents and materials are purchased from BIAcore® AB (Upsala, Sweden). All measurements are performed at 25° C. Samples are dissolved in HBS-EP buffer (150 mM sodium chloride, 3 mM EDTA, 0.05% (w/v) surfactant P-20, and 10 mM HEPES, pH 7.4). To capture Fabs with human kappa, goat-anti-human kappa is immobilized on flow cells 1 to 4 of a CM5 sensor chip at a level of 5000-10000 response units (Rus) using an amine coupling kit. To capture Mabs with mouse IgG1, goat-anti-mouse Fc gamma is immobilized on flow cells 1 to 4 of a CM5 sensor chip at a level of 5000-10000 Rus using an amine coupling kit. To capture antibodies with human IgG4, protein A is immobilized on flow cells 1 to 4 of a CM4 sensor chip at a level of 400-700 Rus using an amine coupling kit. Fabs prepared from E. coli periplasma and Mabs prepared from mammalian cell culture are evaluated using multiple analytical cycles. Each cycle consists of the following steps: 0.3-2 minutes injection of a Fab or a Mab at ~10 µL/minute aiming at a capture of 200-1000 Rus, 2 minutes injection at 50 µL/minute of various concentrations of human hepcidin-25 (from 600 nM to 0.1 nM) obtained as described in Example 1 above followed by 2-10 minutes for dissociation, and regeneration using 30 µL of 10 mM glycine hydrochloride, pH 1.5. The measurements are obtained at 25° C. and the association and dissociation rates for each cycle are evaluated using a "1:1 with mass transfer" binding model in the BIAevaluation software.

The human hepcidin-25 binding parameters of the mouse Fab JXB7 and certain human engineered anti-hepcidin Fabs are shown in Table 5. The human hepcidin-25 binding affinity ($K_D$) of the other human engineered Fabs listed in Table 3 was determined to be between about 214 pM and about 54 pM with each having a $k_{off}$ rate from human hepcidin-25 between about $7.68 \times 10^{-4}$ s$^{-1}$ and about $2.22 \times 10^{-4}$ s$^{-1}$. Therefore, human engineered anti-hepcidin Fabs having a $K_D$ for human hepcidin-25 up to 52-fold lower than that of mouse Fab JXB7 were identified. The human engineered anti-hepcidin Fabs shown in Table 5 comprise the human germline light and heavy chain frameworks O2 and VH1-69, respectively.

TABLE 5

Binding Properties to Human Hepcidin-25

| Fab | $K_{on}$ (M$^{-1}$, s$^{-1}$) | $K_{off}$ (s$^{-1}$) | $K_D$ (M) |
|---|---|---|---|
| JXB7 | 2.49E+06 | 6.98E−03 | 2.80E−9 |
| Hu22 | 7.05E+06 | 4.56E−03 | 6.47E−10 |
| 1.7 | 3.80E+06 | 1.48E−03 | 4.22E−10 |
| 3.12 | 3.94E+06 | 3.47E−04 | 8.83E−11 |
| 3.23 | 3.53E+06 | 2.78E−04 | 7.88E−11 |

The human hepcidin-25 binding parameters of the mouse Mab JXB7 and certain human engineered anti-hepcidin Mabs are shown in Table 6. Therefore, human engineered anti-hepcidin Mabs having a binding affinity ($K_D$) for human hepcidin-25 up to about 33-fold lower than that of the mouse Mab JXB7 were identified. The heavy chain constant regions for Mabs JXB7 and 31B2 are mouse IgG1. The heavy chain constant regions for the other Mabs in Table 6 were human IgG4 (SEQ ID NO: 94).

TABLE 6

Binding to Human Hepcidin-25

| Mab | Kon (M$^{-1}$, s$^{-1}$) | Koff (s$^{-1}$) | Kinetic $K_D$ (M) |
|---|---|---|---|
| JXB7 | 3.70E+07 | 7.37E−03 | 1.99E−9 |
| 31B2 | 1.89E+06 | 1.27E−04 | 7.52E−11 |
| Hu22 | 1.09E+07 | 8.64E−03 | 7.64E−10 |
| 3.23 | 6.20E+06 | 6.59E−04 | 9.94E−11 |
| 3.8 | 5.58E+06 | 7.68E−04 | 1.05E−10 |
| L1.5 | 5.31E+06 | 1.82E−04 | 3.42E−11 |
| 3.12 | 3.68E+06 | 2.20E−04 | 5.99E−11 |

The cynomolgus monkey hepcidin-25 and mouse hepcidin-25 binding parameters of various human engineered anti-hepcidin Mabs are shown in Tables 7 and 8, respectively. Binding to rat hepcidin-25 was undetectable for Mabs Hu22, 3.23, and 3.8. Generally, the Mabs Hu22 and 3.23 were shown to have a $K_D$ for mature cynomolgous monkey hepcidin that was comparable that for human hepcidin-25. However, Mab 3.8 was shown to have a $K_D$ for cynomolgous monkey hepcidin-25 over 10-fold lower than for human hepcidin-25. On the other hand, Mabs Hu22, 3.23, and 3.8 were shown to have a much lower $K_D$ for human hepcidin-25 than for mouse hepcidin-25.

TABLE 7

Binding to Cynomolgus Monkey Hepcidin-25

| Mab | Kon (M$^{-1}$, s$^{-1}$) | Koff (s$^{-1}$) | Kinetic $K_D$ (M) |
|---|---|---|---|
| Hu22 | 8.13E+06 | 8.16E−03 | 9.86E−10 |
| 3.23 | 6.51E+06 | 5.77E−04 | 8.88E−11 |
| 3.8 | 7.07E+06 | 6.60E−04 | 9.33E−12 |

TABLE 8

Binding to Mouse Hepcidin-25

| Mab | Kon (M$^{-1}$, s$^{-1}$) | Koff (s$^{-1}$) | Kinetic $K_D$ (M) |
|---|---|---|---|
| Hu22 | 1.62E+06 | 1.26E−01 | 7.76E−08 |
| 3.23 | 3.83E+06 | 1.92E−01 | 5.01E−08 |
| 3.8 | 3.57E+06 | 1.24E−01 | 3.46E−08 |

Example 3

Cell-Based Assay for Hepcidin-Induced Internalization and Degradation of Ferroportin An in vitro cell based assay may be used to measure the neutralization activity of Mabs directed against human hepcidin. One in vitro cell based assay useful to measure the neutralization activity of the antibodies of the present invention is based on hepcidin-induced internalization and degradation of its receptor, ferroportin. Briefly, a HEK 293 stable cell line is prepared that allows for the inducible expression of ferroportin (FPN). FPN is C-terminally fused with green fluorescent protein (GFP) for tracking purposes. The inducible expression of the FPN-GFP molecule is controlled using the T-REx system, a commercially available tetracycline-regulated expression system without viral transactivators (Invitrogen, Carlsbad, Calif.). The FPN-GFP coding sequence is cloned into pcDNA4/TO vector, which contains an inducible promoter and a Zeocin resistance marker. The resulting construct is transfected into T-REx-293 cells which express the regulatory protein required for doxycycline inducible expression. Zeocin resistant clones are tested for the inducible expression of FPN-GFP. Cell growth conditions are essentially as described in the manufacturer's user manual for the T-REx System. Briefly, cells are grown in DMEM, 10% dialyzed FBS, 20 µM FAC (ferric ammonium citrate), plus 5 µg/mL penicillin-streptomycin. Selection is maintained with 100 µg/mL Zeocin and 5 µg/mL Blasticidin. Cells are plated onto 96-well black/clear plates that are coated with poly-D-lysine. A high resolution fluorescent plate reader is used for reading the total fluorescence per well.

Essentially the assay is run as follows: following trypsinization, 96-well assay plate is seeded with 9,000 cells/well using the FPN-GFP/TREx 293 stable cell line. Seeding volume per well is 80 µl. Cells are allowed to attach overnight. Early the next morning, 9 µl of 30 ng/mL doxycyline is added to each well to induce FPN-GFP expression. This induction is allowed occur for 8 hours. After the induction, media is aspirated media and the wells are washed carefully with 120 µL/well PBS. It is important to remove all liquid from each well as any leftover media will continue to induce expression of FPN-GFP.

The desired treatments are set up in a 96-well format for quick addition to an assay plate after washing. Final assay volume per well is 45 µL. Immediately after adding the treatments, the assay plate is read using the high resolution fluorescent plate reader (set at 550 volts in channel 1). This reading is the 0 hour reading and is used to normalize for cell number per well, which correlates with the total FLU per well. Human hepcidin-25 induced maximal internalization and degradation of ferroportin at 0.5 µM. The IC$_{50}$ for human hepcidin-25 is approximately 8 nM. For anti-hepcidin antibody neutralization assays, the human hepcidin-25 concentration is kept at 100 nM and the anti-hepcidin antibodies are run at 2× dilutions from 0.5 µM to 8 nM. The plates are incubated for 24 hrs, after which, they are read again, and the data is generated as the ratio of total fluorescence units (FLU) per well at 24 hours divided by the total FLU per well at 0 hours.

In this in vitro assay, human hepcidin-25 bioactivity was neutralized with various anti-hepcidin Mabs with an $IC_{50}$ measuring as shown in Table 9.

TABLE 9

In Vitro Neutralization Activity of anti-Hepcidin-25 Human Engineered Mabs

| Mab | $IC_{50}$ (nM) ± Std. Error (n ≥ 4) |
|---|---|
| 3.23 | 59.1 ± 1.2 |
| 3.12 | 62.2 ± 5.9 |
| 3.6 | 54.6 ± 1.5 |
| 3.9 | 51.1 ± 1.8 |
| Hu22 | 163 ± 12.4 |

Example 4

Administration of Anti-hepcidin Monoclonal Antibodies Raise Serum Iron Levels in Cynomolgus Monkeys Treated Subcutaneously with Interleukin-6

The activity of anti-hepcidin antibodies on IL-6 induced serum iron dysregulation in cynomolgus monkeys may be determined as described below.

Briefly, anti-hepcidin antibodies are administered to male cynomolgus monkeys at 1 and 10 mg/kg as an i.v. bolus. Approximately one hour after antibody administration, the animals receive a single subcutaneous administration of human IL-6 at 5 µg/kg. Blood samples are collected at −1 hour (prior to antibody dosing), 0 hour (immediately prior to IL-6 dose) and at 1, 3, 6, 12, 24, 48, 96, 168, 336, 504, and 672 hours following IL-6 treatment. Preferably, each treatment group consists of at least 3 animals. Serum iron levels may be measured by any method known in the art which is generally considered within the medical community to be an acceptable method of measuring serum iron levels.

prior to human IL-6 dose prevents the drop in iron levels due to IL-6 treatment and results in an increase in serum iron of approximately 52% and 108%, respectively, at 3 to 6 hours post IL-6 treatment. After attaining peak levels, the serum iron concentrations subsequently decrease in these two groups and reach levels similar to those of other groups at 24 hours. Both Hu22 ($p<0.01$, 3 and 6 hours) and 3.23 ($p<0.01$, 3, 6, and 12 hours) at 10 mg/kg, produce statistically significant increases of serum iron concentrations relative to IL-6 group with PBS pretreatment. In contrast, neither Hu22 nor 3.23 at 1 mg/kg, result in statistically significant differences in serum iron levels compared to control. Therefore, these results demonstrate that the antibodies of the present invention will be useful in treating anemia resulting from mature hepcidin bioactivity.

Example 5

Determination of Selectivity of Anti-Hepcidin Antibodies Using MALDI-TOF

Clinical routine diagnosis of biomarkers is mostly based on immunological, quantitative techniques—e.g., ELISA. These methods are often not applicable for small antigens or for antigen isoforms (Sparbier, K., International Meeting of the Association of Biomolecular Resource Facilities, Salt Lake City, Utah, Poster V28-S, (2008); and Gutierrez, J. A., et al., (2005)).

Anti-human hepcidin Mab 31B2 is conjugated to CNBr activated sepharose 6 MB resin (GE healthcare, Piscataway, N.J.) according to the manufacturer's protocol. Briefly, the sepharose resin was washed with 1 mM HCl three times and the antibody was diluted into coupling buffer (100 mM NaHCO3, 0.5 M NaCl, pH8.3). Approximately 1.7 mg of antibody was used for conjugation at 4° C. overnight to every mg of resin. Excess antibody was washed away by 0.1 M acetate buffer pH 4. Approximately 100 ml of human serum sample was incubated with 0.8 ml of this sepharose-31B2 resin at 4° C. After overnight incubation, the resin/serum mixture was packed into a column and washed with 10-20

TABLE 10

Anti-Hepcidin Mab Inhibition of IL-6 Induced Decreases in Serum Iron Levels in Cynomolgus Monkeys

| Group | # of Males | Test/Control Articles | Dose Route | Target Dose Level | Target Dose Concentration | Target Dose Volume (mL/kg) |
|---|---|---|---|---|---|---|
| 1 | 3 | 1X PBS | I.V. | 0 mg/kg | 0 mg/mL | 3.3 |
|  |  | 1X PBS with rHSA | S.C. | 0 µg/kg | 0 µg/mL | 1 |
| 2 | 3 | 1X PBS | I.V. | 0 mg/kg | 0 mg/kg | 3.3 |
|  |  | IL-6* | S.C. | 5 µg/kg | 5 µg/mL | 1 |
| 3 | 3 | Hu22 | I.V. | 1 mg/kg | 0.3 mg/mL | 3.3 |
|  |  | IL-6* | S.C. | 5 µg/kg | 5 µg/mL | 1 |
| 4 | 3 | Hu22 | I.V. | 10 mg/kg | 3 mg/mL | 3.3 |
|  |  | IL-6* | S.C. | 5 µg/kg | 5 µg/mL | 1 |
| 5 | 3 | 3.23 | I.V. | 1 mg/kg | 0.3 mg/mL | 3.3 |
|  |  | IL-6* | S.C. | 5 µg/kg | 5 µg/mL | 1 |
| 6 | 3 | 3.23 | I.V. | 10 mg/kg | 3 mg/mL | 3.3 |
|  |  | IL-6* | S.C. | 5 µg/kg | 5 µg/mL | 1 |

*All IL-6 doses are administered in a vehicle consisting of 1X PBS containing 0.1 mg/mL recombinant human serum albumin.
S.C. Subcutaneous injection; given via 1 injection site
I.V. Intravenous; given as an injection via the saphenous vein.

Compared to the PBS control group, human IL-6 treatment produces a transient reduction of serum iron levels, reaching a nadir at 12 hours post IL-6 treatment. Intravenous administration of Hu22 and 3.23 at 10 mg/kg approximately 1 hour column volumes of 10 mM sodium phosphate, 0.5 M NaCl, pH 7.4. The column was washed with 5-10 column volumes of 10 mM sodium phosphate pH 7.4 without NaCl. Finally, the column was eluted with 0.2% TFA. The eluted fractions were analyzed for molecular weights on a Voyager-DE STR instrument (Applied Biosystems, Foster City, Calif.) in linear mode.

For molecular weights smaller than human hepcidin-25, the mass spectrum was generated using a peptide matrix. A dominant peak corresponding to human hepcidin-25, (2790 Dalton) was identified. Less dominant peaks for various truncated forms of hepcidin, namely hepcidin-24 (2674 Dalton), hepcidin-22 (2436 Dalton), and hepcidin-20 (2192 Dalton), were also detectable.

For molecular weights bigger than human hepcidin-25, the mass spectrum was generated using a protein matrix. A dominant peak corresponding to human hepcidin-25 (25 aa, 2790 Dalton) was still identified, but no peak corresponding to prepro-hepcidin (84 aa, 9400 Dalton) or pro-hepcidin (60 aa, 6929 Dalton) was detectable.

Thus, immunoassays using the 31B2 Mab and human engineered versions thereof are selective for human hepcidin-25, the active, most physiologically relevant form of hepcidin in human serum as compared to precursor and/or N-terminally truncated forms thereof known to exist in human serum.

Example 6

Correction of Cryptic Splicing of Anti-Hepcidin-25 Antibody-Encoding mRNA Upon Expression in CHO Cells Standard molecular biology techniques may be used to prepare the recombinant expression vectors, transfect the host cells, select for transformants, isolate host cell lines capable of expressing an antibody of the invention, culture the host cells and recover the expressed antibodies from culture medium. Surprisingly, upon production of the Mabs 3.12 and 3.23 by Chinese hamster ovary (CHO) cell suspension cultures using a recombinant glutamine synthetase (GS) expression system (Lonza Biologics, Inc., Slough, UK), unusually high level of antibody-protein aggregation were observed (~15% and ~30%, as measured by size-exclusion chromatography, respectively). However, a high level of aggregation was not observed when the two Mabs were transiently expressed in human-origin HEK-293 cells. An examination of the mRNA from each of the two CHO cell lines revealed the presence of transcripts of unexpected sizes, suggesting that the nucleotide sequences encoding the antibody proteins of Mabs 3.12 and 3.23 were susceptible to cryptic splicing events. Additionally, an examination of the aggregated protein samples revealed the presence of truncation in the light chain protein. Sequencing of cDNA prepared from mRNA isolated from CHO cells expressing Mabs 3.12 and 3.23 confirmed that the presence of cryptic introns in the light-chain genes. The splice donor was contained in the codons encoding the amino acid residues RATS of LC CDR1 (amino acid 5-7 of SEQ ID NO: 43 and "/" denotes the splice junction, in frame). Furthermore, a probable branch point was found at the codons encoding the amino acid residues L1 of FRL2 (SEQ ID NO: 40) with a probable poly-pyrimidine stretch in the codons encoding the amino acids residues STL and SPL in the LCDR2 of Mab 3.12 and 3.23, respectively. And lastly, the acceptor sites were identified at the codons encoding for the amino acid residues C/Q/Q in LCDR3 of both Mabs 3.12 and 3.23 (amino acids 1-3 of SEQ ID NO: 61; "/" denotes the probable splice junctions).

The original DNA sequences encoding the light chains of Mabs 3.12 and 3.23 (SEQ ID NOs: 153 and 155, respectively) were subsequently modified to eliminate sequences conferring the splice donor, branch point, acceptor and poly-pyrimidine tract to the cryptic intron. More specifically, the donor site was changed from CGC GTA AGT to AGA GTC TCC (SEQ ID NO: 45). The branch point was changed from CTG ATC to CTC ATC (SEQ ID NO: 162); the poly pyrimidine tract from TCC ACC CTG to AGC ACA CTG (SEQ ID NO: 77) and from TCC CCC CTG to AGC CCA CTG (SEQ ID NO: 78) in 3.12 and 3.23, respectively; and the acceptors from TGT CAG CAG TGG to TGC CAA CAA TGG (SEQ ID NO: 100).

Accordingly, subsequent expression of the light chains of Mabs 3.12 and 3.23 was effectuated by recombinant expression vectors harboring the modified DNA sequences as shown in SEQ ID NOs: 12 and 13, respectively. The amount of aggregated antibody produced upon expression of the modified nucleic acid sequences in CHO cells was determined to be 1% or less for both the 3.12 and 3.23 Mabs.

Modifications to the DNA sequences encoding the light chains of various other antibodies of the present invention would likewise be expected to be of great benefit since the splice donor, poly pyrimidine tract, and the splice acceptors are from the codon encoding LCDRs that give specificity to the antibody. The branch point is in FRL2 and the LLIY sequence is highly conserved in light chain frameworks. Moreover, the QQ motif, whose encoding nucleotide sequence spans the identified splice acceptor region, is conserved within the LCDR3 of many of the anti-hepcidin mAbs of the invention. Generally, many light chain germline sequences contain one or both of these Q codons (CAG) that can serve as the acceptor of potential cryptic introns.

We claim:

1. An antibody that comprises six CDRs selected from the group consisting of:
   (i) LCDR1, LCDR2, LCDR3, HCDR1, HCDR2, and HCDR3 having the amino acid sequences as shown in SEQ ID NOs: 41, 53, 31, 63, 84, and 46, respectively;
   (ii) LCDR1, LCDR2, LCDR3, HCDR1, HCDR2, and HCDR3 having the amino acid sequences as shown in SEQ ID NOs: 43, 30, 31, 32, 44, and 46, respectively;
   (iii) LCDR1, LCDR2, LCDR3, HCDR1, HCDR2, and HCDR3 having the amino acid sequences as shown in SEQ ID NOs: 43, 53, 61, 63, 85, and 46, respectively; and
   (iv) LCDR1, LCDR2, LCDR3, HCDR1, HCDR2, and HCDR3 having the amino acid sequences as shown in SEQ ID NOs: 43, 57, 61, 63, 84, and 46, respectively.

2. A method of increasing serum iron levels, reticulocyte count, red blood cell count, hemoglobin, and/or hematocrit comprising administering to a subject an effective amount of the antibody of claim 1.

3. A method of treating anemia in a subject, comprising administering to the subject an effective amount of the antibody of claim 1.

4. A pharmaceutical composition comprising the antibody of claim 1, and a pharmaceutically acceptable carrier, diluent, or excipient.

5. An immunoassay comprising a) obtaining a sample to be assayed for human mature hepcidin; b) contacting the sample with an antibody of claim 1 under suitable conditions for antibody binding and allowing any human mature hepcidin present to form a complex with the antibody; and c) detecting the presence or absence of the complex; and/or determining the amount of the complex in the sample by an immunodetection method.

* * * * *

SEQUENCE LISTING

```
<160> NUMBER OF SEQ ID NOS: 162

<210> SEQ ID NO 1
<211> LENGTH: 25
<212> TYPE: PRT
<213> ORGANISM: Homo sapiens

<400> SEQUENCE: 1

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 2
```

```
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 2
caggtgcagc tggtgcagtc tggggctgag gtgaagaagc ctgggtcctc agtgaaggtt      60
tcctgcaagg catctggcta caccttcctg atttatccaa taagctgggt gcgacaggcc     120
cctggacaag ggcttgagtg gatgggaaat tttcatcctt acctgggtgt cactaactac     180
ctggaaaagt tcaagggcag agtcaccatt accgcggaca atccacgag cacagcctac      240 atggagctga gcagcctgag atctgaggac acggccgtgt attactgtgc gcgcggggg     300 actgggtcct ttgactactg gggccaagga accacggtca ccgtctcctc agcctccacc     360
aagggcccat cggtcttccc gctagcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccctgccc agcacctgag ttcctggggg gaccatcagt cttcctgttc     720
cccccaaaac ccaaggacac tctcatgatc tcccggaccc ctgaggtcac gtgcgtggtg     780
gtggacgtga gccaggaaga cccccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtc     960
tccaacaaag gcctcccgtc ctccatcgag aaaaccatct ccaaagccaa agggcagccc    1020
cgagagccac aggtgtacac cctgccccca tcccaggagg agatgaccaa gaaccaggtc    1080
agcctgacct gcctggtcaa aggcttctac cccagcgaca tcgccgtgga gtgggaaagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggt                                                            1329

<210> SEQ ID NO 3
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 3
caggtgcagc tggtgcagtc tggggctgag gtgaagaagc ctgggtcctc agtgaaggtt      60
tcctgcaagg catctggcta caccttcact atttatccaa taagctgggt gcgacaggcc     120
cctggacaag ggcttgagtg gatgggaaat tttcatcctt acctgggtga cactaactac     180
aatgaaaagt tcaagggcag agtcaccatt accgcggaca atccacgag cacagcctac      240 atggagctga gcagcctgag atctgaggac acggccgtgt attactgtgc gcgcggggg     300 actgggtcct ttgactactg gggccaagga accacggtca ccgtctcctc agcctccacc     360
aagggcccat cggtcttccc gctagcgccc tgctccagga gcacctccga gagcacagcc     420
gccctgggct gcctggtcaa ggactacttc cccgaaccgg tgacggtgtc gtggaactca     480
```

```
ggcgccctga ccagcggcgt gcacaccttc ccggctgtcc tacagtcctc aggactctac    540
tccctcagca gcgtggtgac cgtgccctcc agcagcttgg gcacgaagac ctacacctgc    600
aacgtagatc acaagcccag caacaccaag gtggacaaga gagttgagtc caaatatggt    660
cccccatgcc caccctgccc agcacctgag ttcctggggg gaccatcagt cttcctgttc    720
cccccaaaac ccaaggacac tctcatgatc tcccggaccc ctgaggtcac gtgcgtggtg    780
gtggacgtga gccaggaaga ccccgaggtc cagttcaact ggtacgtgga tggcgtggag    840
gtgcataatg ccaagacaaa gccgcgggag gagcagttca acagcacgta ccgtgtggtc    900
agcgtcctca ccgtcctgca ccaggactgg ctgaacggca aggagtacaa gtgcaaggtc    960
tccaacaaag gctcccgtc ctccatcgag aaaaccatct ccaaagccaa agggcagccc   1020
cgagagccac aggtgtacac cctgccccca tcccaggagg agatgaccaa gaaccaggtc   1080
agcctgacct gcctggtcaa aggcttctac cccagcgaca tcgccgtgga gtgggaaagc   1140
aatgggcagc cggagaacaa ctacaagacc acgcctcccg tgctggactc cgacggctcc   1200
ttcttcctct acagcaggct aaccgtggac aagagcaggt ggcaggaggg gaatgtcttc   1260
tcatgctccg tgatgcatga ggctctgcac aaccactaca cacagaagag cctctccctg   1320
tctctgggt                                                          1329
```

<210> SEQ ID NO 4
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 4

```
caggtgcagc tggtgcagtc tggggctgag gtgaagaagc ctgggtcctc agtgaaggtt     60
tcctgcaagg catctggcta caccttcctg atttatccaa taagctgggt gcgacaggcc    120
cctggacaag ggcttgagtg gatgggaaat tttcatcctt acctgggtgt cactaactac    180
ctggaaaagt tcaagggcag agtcaccatt accgcggaca atccacgag cacagcctac    240 atggagctga gcagcctgag atctgaggac acggccgtgt attactgtgc gcgcggggg    300 actgggtcct ttgactactg gggccaagga accacggtca ccgtctcctc agcctccacc    360
aagggcccat cggtcttccc gctagcgccc tgctccagga gcacctccga gagcacagcc    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacgaagac ctacacctgc    600
aacgtagatc acaagcccag caacaccaag gtggacaaga gagttgagtc caaatatggt    660
cccccatgcc caccctgccc agcacctgag ttcctggggg gaccatcagt cttcctgttc    720
cccccaaaac ccaaggacac tctcatgatc tcccggaccc ctgaggtcac gtgcgtggtg    780
gtggacgtga gccaggaaga ccccgaggtc cagttcaact ggtacgtgga tggcgtggag    840
gtgcataatg ccaagacaaa gccgcgggag gagcagttca acagcacgta ccgtgtggtc    900
agcgtcctca ccgtcctgca ccaggactgg ctgaacggca aggagtacaa gtgcaaggtc    960
tccaacaaag gctcccgtc ctccatcgag aaaaccatct ccaaagccaa agggcagccc   1020
cgagagccac aggtgtacac cctgccccca tcccaggagg agatgaccaa gaaccaggtc   1080
agcctgacct gcctggtcaa aggcttctac cccagcgaca tcgccgtgga gtgggaaagc   1140
```

| aatgggcagc cggagaacaa ctacaagacc acgcctcccg tgctggactc cgacggctcc | 1200 |
| ttcttcctct acagcaggct aaccgtggac aagagcaggt ggcaggaggg gaatgtcttc | 1260 |
| tcatgctccg tgatgcatga ggctctgcac aaccactaca cacagaagag cctctccctg | 1320 |
| tctctgggt | 1329 |

<210> SEQ ID NO 5
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 5

| caggtgcagc tggtgcagtc tggggctgag gtgaagaagc ctgggtcctc agtgaaggtt | 60 |
| tcctgcaagg catctggcta caccttcctg atttatccaa taagctgggt gcgacaggcc | 120 |
| cctggacaag gcttgagtg gatgggaaat tttcatcctt acctgggtgt cactaactac | 180 |
| gtggaaaagt tcaagggcag agtcaccatt accgcgaca atccacgag cacagcctac | 240 |
| atggagctga gcagcctgag atctgaggac acggccgtgt attactgtgc gcgcgggggg | 300 |
| actgggtcct tgactactg gggccaagga accacggtca ccgtctcctc agcctccacc | 360 |
| aagggcccat cggtcttccc gctagcgccc tgctccagga gcacctccga gagcacagcc | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacgaagac ctacacctgc | 600 |
| aacgtagatc acaagcccag caacaccaag gtggacaaga gagttgagtc caaatatggt | 660 |
| cccccatgcc caccctgccc agcacctgag ttcctggggg gaccatcagt cttcctgttc | 720 |
| cccccaaaac ccaaggacac tctcatgatc tcccggaccc ctgaggtcac gtgcgtggtg | 780 |
| gtggacgtga gccaggaaga ccccgaggtc cagttcaact ggtacgtgga tggcgtggag | 840 |
| gtgcataatg ccaagacaaa gccgcgggag gagcagttca acagcacgta ccgtgtggtc | 900 |
| agcgtcctca ccgtcctgca ccaggactgg ctgaacggca aggagtacaa gtgcaaggtc | 960 |
| tccaacaaag gcctcccgtc ctccatcgag aaaaccatct ccaaagccaa agggcagccc | 1020 |
| cgagagccac aggtgtacac cctgccccca tcccaggagg agatgaccaa gaaccaggtc | 1080 |
| agcctgacct gcctggtcaa aggcttctac cccagcgaca tcgccgtgga gtgggaaagc | 1140 |
| aatgggcagc cggagaacaa ctacaagacc acgcctcccg tgctggactc cgacggctcc | 1200 |
| ttcttcctct acagcaggct aaccgtggac aagagcaggt ggcaggaggg gaatgtcttc | 1260 |
| tcatgctccg tgatgcatga ggctctgcac aaccactaca cacagaagag cctctccctg | 1320 |
| tctctgggt | 1329 |

<210> SEQ ID NO 6
<211> LENGTH: 443
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
    35                  40                  45
Gly Asn Phe His Pro Tyr Leu Gly Val Thr Asn Tyr Leu Glu Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Thr Gly Ser Phe Asp Tyr Trp Gly Gln Gly Thr Thr
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly
        435                 440

<210> SEQ ID NO 7
<211> LENGTH: 443
<212> TYPE: PRT
<213> ORGANISM: Artificial Sequence
<220> FEATURE:
<223> OTHER INFORMATION: Synthetic Construct

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365
```

```
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly
        435                 440
```

<210> SEQ ID NO 8
<211> LENGTH: 443
<212> TYPE: PRT
<213> ORGANISM: Artificial Sequence
<220> FEATURE:
<223> OTHER INFORMATION: Synthetic Construct

<400> SEQUENCE: 8

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Leu Ile Tyr
            20                  25                  30
Pro Ile Ser Trp Val Arg Gln Ala Pro Gly Gln Gly Leu Glu Trp Met
        35                  40                  45
Gly Asn Phe His Pro Tyr Leu Gly Val Thr Asn Tyr Leu Glu Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Thr Gly Ser Phe Asp Tyr Trp Gly Gln Gly Thr Thr
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
    210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
```

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
                435                 440

<210> SEQ ID NO 9
<211> LENGTH: 443
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
                20                  25                  30

Pro Ile Ser Trp Val Arg Gln Ala Pro Gly Gln Gly Leu Glu Trp Met
                35                  40                  45

Gly Asn Phe His Pro Tyr Leu Gly Val Thr Asn Tyr Val Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
                100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser Gln Glu Asp Pro Glu Val Gln Phe
                260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly
        435                 440

<210> SEQ ID NO 10
<211> LENGTH: 645
<212> TYPE: DNA
<213> ORGANISM: Artificial Sequence
<220> FEATURE:
<223> OTHER INFORMATION: Synthetic Construct

<400> SEQUENCE: 10
gacatccaga tgacccagtc tccatcctcc ctgtctgcat ctgtaggaga cagagtcacc      60
atcacttgca gtgccgagtc acgcgtaagt tccacttact tgttctggta tcagcagaaa     120
ccagggaaag cccctaagct cctgatctat aggacatccc cctggcttc tggagtccca      180
tcaaggttca gtggcagtgg atctgggaca gatttcactc tcaccatcag cagtctgcaa     240
cctgaagatt ttgcaactta ctattgtcag cagtggagtg gttacccatt acgttcggc      300
ggagggacca aggtggagat caaacggact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag      600
ggcctgagct cgcccgtcac aaagagcttc aacaggggag agtgc                     645

<210> SEQ ID NO 11

```
<211> LENGTH: 645
<212> TYPE: DNA
<213> ORGANISM: Artificial Sequence
<220> FEATURE:
<223> OTHER INFORMATION: Synthetic Construct

<400> SEQUENCE: 11
gacatccaga tgacccagtc tccatcctcc ctgtctgcat ctgtaggaga cagagtcacc      60
atcacttgca gtgccagctc acgcgtaagt tccacttact tgttctggta tcagcagaaa     120
ccagggaaag cccctaagct cctgatctat aggacatcca cctggcttc tggagtccca     180
tcaaggttca gtggcagtgg atctgggaca gatttcactc tcaccatcag cagtctgcaa     240
cctgaagatt ttgcaactta ctattgtcag cagtggagtg gttacccatt cacgttcggc     300
ggagggacca aggtggagat caaacggact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgc                    645

<210> SEQ ID NO 12
<211> LENGTH: 645
<212> TYPE: DNA
<213> ORGANISM: Artificial Sequence
<220> FEATURE:
<223> OTHER INFORMATION: Synthetic Construct

<400> SEQUENCE: 12
gacatccaga tgacccagtc tccatcctcc ctgtctgcat ctgtaggaga cagagtcacc      60
atcacttgca gtgccagctc aagagtctcc tccacttact tgttctggta tcagcagaaa     120
ccagggaaag cccctaagct cctcatctat aggacaagca cactgacctc tggagtccca     180
tcaaggttca gtggcagtgg atctgggaca gatttcactc tcaccatcag cagtctgcaa     240
cctgaagatt ttgcaactta ctattgccaa caatggagtg gttacccatt cgtgttcggc     300
ggagggacca aggtggagat caaacggact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgc                    645

<210> SEQ ID NO 13
<211> LENGTH: 645
<212> TYPE: DNA
<213> ORGANISM: Artificial Sequence
<220> FEATURE:
<223> OTHER INFORMATION: Synthetic Construct

<400> SEQUENCE: 13
gacatccaga tgacccagtc tccatcctcc ctgtctgcat ctgtaggaga cagagtcacc      60
atcacttgca gtgccagctc aagagtctcc tccacttact tgttctggta tcagcagaaa     120
ccagggaaag cccctaagct cctcatctat aggacaagcc cactggcctc tggagtccca     180
tcaaggttca gtggcagtgg atctgggaca gatttcactc tcaccatcag cagtctgcaa     240
```

```
cctgaagatt tgcaactta ctattgccaa caatggagtg gttacccatt cgtgttcggc      300
ggagggacca aggtggagat caaacggact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagacta cgagaaacac aaagtctacg cctgcgaagt cacccatcag      600
ggcctgagct cgcccgtcac aaagagcttc aacaggggag agtgc                     645
```

```
<210> SEQ ID NO 14
<211> LENGTH: 215
<212> TYPE: PRT
<213> ORGANISM: Artificial Sequence
<220> FEATURE:
<223> OTHER INFORMATION: Synthetic Construct

<400> SEQUENCE: 14
```

Asp Ile Gln Met Thr Gln Ser Pro Ser Ser Leu Ser Ala Ser Val Gly
1               5                   10                  15

Asp Arg Val Thr Ile Thr Cys Ser Ala Glu Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 15
<211> LENGTH: 215
<212> TYPE: PRT
<213> ORGANISM: Artificial Sequence
<220> FEATURE:
<223> OTHER INFORMATION: Synthetic Construct

<400> SEQUENCE: 15
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 16
<211> LENGTH: 215
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Thr Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 17
<211> LENGTH: 215
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 18
<211> LENGTH: 25
<212> TYPE: PRT
<213> ORGANISM: Bos sp.

<400> SEQUENCE: 18

Asp Thr His Phe Pro Ile Cys Ile Phe Cys Cys Gly Cys Cys Arg Lys
1               5                   10                  15

Gly Thr Cys Gly Met Cys Cys Arg Thr
            20                  25
```

<210> SEQ ID NO 19
<211> LENGTH: 25
<212> TYPE: PRT
<213> ORGANISM: Sus sp.

<400> SEQUENCE: 19

Asp Thr His Phe Pro Ile Cys Ile Phe Cys Cys Gly Cys Cys Arg Lys
1               5                   10                  15

Ala Ile Cys Gly Met Cys Cys Lys Thr
            20                  25

<210> SEQ ID NO 20
<211> LENGTH: 25
<212> TYPE: PRT
<213> ORGANISM: Macaca sp.

<400> SEQUENCE: 20

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 21
<211> LENGTH: 25
<212> TYPE: PRT
<213> ORGANISM: Canis sp.

<400> SEQUENCE: 21

Asp Thr His Phe Pro Ile Cys Ile Phe Cys Cys Gly Cys Cys Lys Thr
1               5                   10                  15

Pro Lys Cys Gly Leu Cys Cys Lys Thr
            20                  25

<210> SEQ ID NO 22
<211> LENGTH: 25
<212> TYPE: PRT
<213> ORGANISM: Mus sp.

<400> SEQUENCE: 22

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 23
<211> LENGTH: 25
<212> TYPE: PRT
<213> ORGANISM: Rattus sp.

<400> SEQUENCE: 23

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Asp Thr Phe Pro Ile Cys Ile Phe Cys Cys Cys Cys Gly Cys Cys
1               5                   10                  15

Thr

<210> SEQ ID NO 25
<211> LENGTH: 571
<212> TYPE: PRT
<213> ORGANISM: Homo sapiens

<400> SEQUENCE: 25

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
                20                  25                  30

Ser Leu Ser Thr Trp Gly Asp Arg Met Trp His Phe Ala Val Ser Val
            35                  40                  45

Phe Leu Val Glu Leu Tyr Gly Asn Ser Leu Leu Leu Thr Ala Val Tyr
        50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
                100                 105                 110

Val Phe Leu His Lys His Glu Leu Leu Thr Met Tyr His Gly Trp Val
            115                 120                 125

Leu Thr Ser Cys Tyr Ile Leu Ile Ile Thr Ile Ala Asn Ile Ala Asn
        130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
                180                 185                 190

Gly Gln Ile Met Thr Phe Gly Ser Pro Val Ile Gly Cys Gly Phe Ile
            195                 200                 205

Ser Gly Trp Asn Leu Val Ser Met Cys Val Glu Tyr Val Leu Leu Trp
        210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
                260                 265                 270

Ile His Glu Leu Glu His Glu Gln Glu Pro Thr Cys Ala Ser Gln Met
            275                 280                 285

Ala Glu Pro Phe Arg Thr Phe Arg Asp Gly Trp Val Ser Tyr Tyr Asn
        290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
                340                 345                 350

```
Gly Ile Met Gly Thr Val Ala Phe Thr Trp Leu Arg Arg Lys Cys Gly
            355                 360                 365

Leu Val Arg Thr Gly Leu Ile Ser Gly Leu Ala Gln Leu Ser Cys Leu
370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
            405                 410                 415

Ser Ile Thr Pro Thr Lys Ile Pro Glu Ile Thr Thr Glu Ile Tyr Met
            420                 425                 430

Ser Asn Gly Ser Asn Ser Ala Asn Ile Val Pro Glu Thr Ser Pro Glu
            435                 440                 445

Ser Val Pro Ile Ile Ser Val Ser Leu Leu Phe Ala Gly Val Ile Ala
450                 455                 460

Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
                485                 490                 495

Asn Ser Met Asn Tyr Leu Leu Asp Leu Leu His Phe Ile Met Val Ile
                500                 505                 510

Leu Ala Pro Asn Pro Glu Ala Phe Gly Leu Leu Val Leu Ile Ser Val
            515                 520                 525

Ser Phe Val Ala Met Gly His Ile Met Tyr Phe Arg Phe Ala Gln Asn
530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Ser Ala Ser Ser Ser Val Ser Ser Thr Tyr Leu His
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Gly Tyr Thr Phe Thr Ile Tyr Pro Ile Glu
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28
```

```
Asn Phe His Pro Tyr Asn Gly Asp Thr Asn Tyr Asn Glu Lys Phe Lys
1               5                   10                  15

Gly

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Gly Tyr Thr Phe Tyr Ile Tyr Pro Ile Ser
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Arg Thr Ser Thr Leu Ala Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Gln Gln Trp Ser Gly Tyr Pro Phe Thr
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Tyr Thr Phe Thr Ile Tyr Pro Ile Ser
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct

<400> SEQUENCE: 33

Asn Phe His Pro Tyr Lys Gly Leu Thr Asn Tyr Asn Glu Lys Phe Lys
1               5                   10                  15

Gly

<210> SEQ ID NO 34
<211> LENGTH: 61
<212> TYPE: PRT
<213> ORGANISM: Homo sapiens

<400> SEQUENCE: 34
```

```
Gly Ser Val Phe Pro Gln Gln Thr Gly Gln Leu Ala Glu Leu Gln Pro
1               5                   10                  15

Gln Asp Arg Ala Gly Ala Arg Ala Ser Trp Met Pro Met Phe Gln Arg
            20                  25                  30

Arg Arg Arg Arg Asp Thr His Phe Pro Ile Cys Ile Phe Cys Cys Gly
        35                  40                  45

Cys Cys His Arg Ser Lys Cys Gly Met Cys Cys Lys Thr
    50                  55                  60
```

<210> SEQ ID NO 35
<211> LENGTH: 25
<212> TYPE: PRT
<213> ORGANISM: Homo sapiens

<400> SEQUENCE: 35

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 36
<211> LENGTH: 14
<212> TYPE: PRT
<213> ORGANISM: Homo sapiens

<400> SEQUENCE: 36

```
Trp Val Arg Gln Ala Pro Gly Gln Gly Leu Glu Trp Met Gly
1               5                   10
```

<210> SEQ ID NO 37
<211> LENGTH: 32
<212> TYPE: PRT
<213> ORGANISM: Homo sapiens

<400> SEQUENCE: 37

```
Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 38
<211> LENGTH: 11
<212> TYPE: PRT
<213> ORGANISM: Homo sapiens

<400> SEQUENCE: 38

```
Trp Gly Gln Gly Thr Thr Val Thr Val Ser Ser
1               5                   10
```

<210> SEQ ID NO 39
<211> LENGTH: 23
<212> TYPE: PRT
<213> ORGANISM: Homo sapiens

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 40

```
<211> LENGTH: 15
<212> TYPE: PRT
<213> ORGANISM: Homo sapiens

<400> SEQUENCE: 40

Trp Tyr Gln Gln Lys Pro Gly Lys Ala Pro Lys Leu Leu Ile Tyr
1               5                   10                  15

<210> SEQ ID NO 41
<211> LENGTH: 12
<212> TYPE: PRT
<213> ORGANISM: Artificial Sequence
<220> FEATURE:
<223> OTHER INFORMATION: Synthetic Construct

<400> SEQUENCE: 41

Ser Ala Glu Ser Arg Val Ser Ser Thr Tyr Leu Phe
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa at position 3 = Glu or Ser

<400> SEQUENCE: 42

Ser Ala Xaa Ser Arg Val Ser Ser Thr Tyr Leu Phe
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic Construct

<400> SEQUENCE: 43

Ser Ala Ser Ser Arg Val Ser Ser Thr Tyr Leu Phe
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Asn Phe His Pro Tyr Leu Gly Asp Thr Asn Tyr Asn Glu Lys Phe Lys
1               5                   10                  15

Gly

<210> SEQ ID NO 45
<211> LENGTH: 9
<212> TYPE: DNA
<213> ORGANISM: Artificial Sequence
<220> FEATURE:
<223> OTHER INFORMATION: Synthetic Construct

<400> SEQUENCE: 45 agagtctcc                                                                9
```

```
<210> SEQ ID NO 46
<211> LENGTH: 8
<212> TYPE: PRT
<213> ORGANISM: Artificial Sequence
<220> FEATURE:
<223> OTHER INFORMATION: Synthetic Construct

<400> SEQUENCE: 46

Gly Gly Thr Gly Ser Phe Asp Tyr
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct

<400> SEQUENCE: 47

Ser Leu Ser Ser Arg Val Ser Ser Thr Tyr Leu Phe
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic Construct

<400> SEQUENCE: 48

Ser Ile Ser Ser Arg Val Ser Ser Thr Tyr Leu Phe
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic Construct

<400> SEQUENCE: 49

Ser Trp Ser Ser Arg Val Ser Ser Thr Tyr Leu Phe
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Ser Ala Gly Ser Arg Val Ser Ser Thr Tyr Leu Phe
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Construct

<400> SEQUENCE: 51

Ser Ala Ser Ser Arg Val Val Ser Thr Tyr Leu Phe
1               5                   10
```

```
<210> SEQ ID NO 52
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 = Ala, Leu, or Ile
<220> FEATURE:
<221> NAME/KEY: MISC_FEATURE
<222> LOCATION: (3)..(3)
<223> OTHER INFORMATION: Xaa at position 3 = Ser or Gly
<220> FEATURE:
<221> NAME/KEY: MISC_FEATURE
<222> LOCATION: (5)..(5)
<223> OTHER INFORMATION: Xaa at position 5 = Arg or Ser

<400> SEQUENCE: 52

Ser Xaa Xaa Ser Xaa Val Ser Ser Thr Tyr Leu Phe
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Arg Thr Ser Pro Leu Ala Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Arg Thr Ser Ala Leu Ala Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Construct

<400> SEQUENCE: 55

Arg Thr Ser Trp Leu Ala Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct

<400> SEQUENCE: 56

Arg Thr Ser Thr Gly Ala Ser
1               5

<210> SEQ ID NO 57
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 57

Arg Thr Ser Thr Leu Thr Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Arg Thr Ser Thr Leu Val Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct

<400> SEQUENCE: 59

Arg Thr Ser Thr Leu Leu Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 = Thr, Pro, or Ala
<220> FEATURE:
<221> NAME/KEY: MISC_FEATURE
<222> LOCATION: (5)..(5)
<223> OTHER INFORMATION: Xaa at position 5 = Leu or Gly
<220> FEATURE:
<221> NAME/KEY: MISC_FEATURE
<222> LOCATION: (6)..(6)
<223> OTHER INFORMATION: Xaa at position 6 = Ala, Thr, or Val

<400> SEQUENCE: 60

Arg Thr Ser Xaa Xaa Xaa Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Gln Trp Ser Gly Tyr Pro Phe Val
1               5

<210> SEQ ID NO 62
<211> LENGTH: 9
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa at position 9 = Thr or Val

<400> SEQUENCE: 62

Gln Gln Trp Ser Gly Tyr Pro Phe Xaa
1               5

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Gly Tyr Thr Phe Leu Ile Tyr Pro Ile Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Gly Tyr Thr Phe Trp Ile Tyr Pro Ile Ser
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa at position 5 = Thr, Trp, Tyr, or Leu
<220> FEATURE:
<221> NAME/KEY: MISC_FEATURE
<222> LOCATION: (10)..(10)
<223> OTHER INFORMATION: Xaa at position 10 = Ser or Glu

<400> SEQUENCE: 65

Gly Tyr Thr Phe Xaa Ile Tyr Pro Ile Xaa
1               5                   10

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

Asn Phe His Pro Tyr Leu Gly Thr Thr Asn Tyr Asn Glu Lys Phe Lys
1               5                   10                  15

Gly

<210> SEQ ID NO 67
<211> LENGTH: 17
<212> TYPE: PRT
<213> ORGANISM: Artificial Sequence
```

```
<220> FEATURE:
<223> OTHER INFORMATION: Synthetic Construct

<400> SEQUENCE: 67

Asn Phe His Pro Tyr Leu Gly Leu Thr Asn Tyr Asn Glu Lys Phe Lys
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Synthetic Construct

<400> SEQUENCE: 68

Asn Phe His Pro Tyr Leu Gly Val Thr Asn Tyr Asn Glu Lys Phe Lys
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: Synthetic Construct

<400> SEQUENCE: 69

Asn Phe His Pro Tyr Leu Gly Met Thr Asn Tyr Asn Glu Lys Phe Lys
1               5                   10                  15

Gly

<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Asn Phe His Pro Tyr Leu Gly Asp Ala Asn Tyr Asn Glu Lys Phe Lys
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa at position 8 = Asp, Thr, Leu, or Val
<220> FEATURE:
<221> NAME/KEY: MISC_FEATURE
<222> LOCATION: (9)..(9)
<223> OTHER INFORMATION: Xaa at position 9 = Thr or Ala

<400> SEQUENCE: 71

Asn Phe His Pro Tyr Leu Gly Xaa Xaa Asn Tyr Asn Glu Lys Phe Lys
1               5                   10                  15

Gly
```

```
<210> SEQ ID NO 72
<211> LENGTH: 8
<212> TYPE: PRT
<213> ORGANISM: Artificial Sequence
<220> FEATURE:
<223> OTHER INFORMATION: Synthetic Construct

<400> SEQUENCE: 72

Gly Gly Phe Gly Ser Phe Asp Tyr
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Construct

<400> SEQUENCE: 73

Gly Gly Thr Gly Ala Phe Asp Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

Gly Gly Thr Gly Ser Phe Pro Tyr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa at position 3 = Thr or Phe
<220> FEATURE:
<221> NAME/KEY: MISC_FEATURE
<222> LOCATION: (5)..(5)
<223> OTHER INFORMATION: Xaa at position 5 = Ser or Ala
<220> FEATURE:
<221> NAME/KEY: MISC_FEATURE
<222> LOCATION: (7)..(7)
<223> OTHER INFORMATION: Xaa at position 7 = Asp or Pro

<400> SEQUENCE: 75

Gly Gly Xaa Gly Xaa Phe Xaa Tyr
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 = Pro or Thr
<220> FEATURE:
<221> NAME/KEY: MISC_FEATURE
<222> LOCATION: (6)..(6)
<223> OTHER INFORMATION: Xaa at position 6 = Ala, Thr, or Leu
```

```
<400> SEQUENCE: 76

Arg Thr Ser Xaa Leu Xaa Ser
1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic Construct

<400> SEQUENCE: 77 agcacactg                                                                 9

<210> SEQ ID NO 78
<211> LENGTH: 9
<212> TYPE: DNA
<213> ORGANISM: Artificial Sequence
<220> FEATURE:
<223> OTHER INFORMATION: Synthetic Construct

<400> SEQUENCE: 78 agcccactg                                                                 9

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa at position 3 = Thr or Glu
<220> FEATURE:
<221> NAME/KEY: MISC_FEATURE
<222> LOCATION: (5)..(5)
<223> OTHER INFORMATION: Xaa at position 5 = Leu or Thr

<400> SEQUENCE: 79

Gly Tyr Xaa Phe Xaa Ile Tyr Pro Ile
1               5

<210> SEQ ID NO 80
<211> LENGTH: 17
<212> TYPE: PRT
<213> ORGANISM: Artificial Sequence
<220> FEATURE:
<223> OTHER INFORMATION: Synthetic Construct

<400> SEQUENCE: 80

Asn Phe His Pro Tyr Leu Gly Asp Thr Lys Tyr Val Glu Lys Phe Lys
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: Synthetic Construct

<400> SEQUENCE: 81

Asn Phe His Pro Tyr Leu Gly Asp Thr Arg Tyr Val Glu Lys Phe Lys
1               5                   10                  15

Gly
```

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct

<400> SEQUENCE: 82

Asn Phe His Pro Tyr Leu Gly Val Thr Lys Tyr Leu Glu Lys Phe Lys
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: Synthetic Construct

<400> SEQUENCE: 83

Asn Phe His Pro Tyr Leu Gly Val Thr Lys Tyr Val Glu Lys Phe Lys
1               5                   10                  15

Gly

<210> SEQ ID NO 84
<211> LENGTH: 17
<212> TYPE: PRT
<213> ORGANISM: Artificial Sequence
<220> FEATURE:
<223> OTHER INFORMATION: Synthetic Construct

<400> SEQUENCE: 84

Asn Phe His Pro Tyr Leu Gly Val Thr Asn Tyr Leu Glu Lys Phe Lys
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: Synthetic Construct

<400> SEQUENCE: 85

Asn Phe His Pro Tyr Leu Gly Val Thr Asn Tyr Val Glu Lys Phe Lys
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: Synthetic Construct

<400> SEQUENCE: 86

Asn Phe His Pro Tyr Leu Gly Asp Thr Asn Tyr Leu Glu Lys Phe Lys
1               5                   10                  15

Gly

<210> SEQ ID NO 87
<211> LENGTH: 17

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa at position 8 = Val or Asp
<220> FEATURE:
<221> NAME/KEY: MISC_FEATURE
<222> LOCATION: (10)..(10)
<223> OTHER INFORMATION: Xaa at position 10 = Asn, Lys, or Arg
<220> FEATURE:
<221> NAME/KEY: MISC_FEATURE
<222> LOCATION: (12)..(12)
<223> OTHER INFORMATION: Xaa at position 12 = Val, Leu, or Asn

<400> SEQUENCE: 87

Asn Phe His Pro Tyr Leu Gly Xaa Thr Xaa Tyr Xaa Glu Lys Phe Lys
1               5                   10                  15

Gly

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Gln Gln Trp Ser Gly Tyr Pro Phe Thr
1               5

<210> SEQ ID NO 89
<211> LENGTH: 107
<212> TYPE: PRT
<213> ORGANISM: Homo sapiens

<400> SEQUENCE: 89

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 90
<211> LENGTH: 329
<212> TYPE: PRT
<213> ORGANISM: Homo sapiens

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 91
<211> LENGTH: 329
<212> TYPE: PRT
<213> ORGANISM: Homo sapiens

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 92
<211> LENGTH: 325
<212> TYPE: PRT
<213> ORGANISM: Homo sapiens

<400> SEQUENCE: 92

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 93
<211> LENGTH: 326
<212> TYPE: PRT
<213> ORGANISM: Artificial Sequence
<220> FEATURE:
<223> OTHER INFORMATION: Synthetic Construct

<400> SEQUENCE: 93

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

-continued

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 94
<211> LENGTH: 326
<212> TYPE: PRT
<213> ORGANISM: Artificial Sequence
<220> FEATURE:
<223> OTHER INFORMATION: Synthetic Construct

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 95
<211> LENGTH: 97
<212> TYPE: PRT
<213> ORGANISM: Artificial Sequence
<220> FEATURE:
<223> OTHER INFORMATION: Synthetic Construct

<400> SEQUENCE: 95

Met Gly Ser Ser His His His His His Ser Ser Gly Leu Val Pro
1               5                   10                  15

Arg Gly Ser His Met Ala Ser Met Thr Gly Gln Gln Met Gly Arg
            20                  25                  30

Gly Ser Ala Val Tyr Ile Ala Trp Pro Leu Gln Gly Trp Gln Ala Thr
        35                  40                  45

Phe Gly Gly Gly Asp His Pro Pro Lys Ser Asp Leu Ile Glu Gly Arg
    50                  55                  60

Gly Ile Leu Asp Asp Asp Lys Asp Thr His Phe Pro Ile Cys Ile
65                  70                  75                  80

Phe Cys Cys Gly Cys Cys His Arg Ser Lys Cys Gly Met Cys Cys Lys
                85                  90                  95

Thr

<210> SEQ ID NO 96
<211> LENGTH: 32
<212> TYPE: PRT
<213> ORGANISM: Homo sapiens

<400> SEQUENCE: 96

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 97
<211> LENGTH: 10
<212> TYPE: PRT
<213> ORGANISM: Homo sapiens
```

<400> SEQUENCE: 97

Phe Gly Gly Gly Thr Lys Val Glu Ile Lys
1               5                   10

<210> SEQ ID NO 98
<211> LENGTH: 117
<212> TYPE: PRT
<213> ORGANISM: Mus sp.

<400> SEQUENCE: 98

Gln Val His Leu Gln Gln Ser Gly Ala Glu Leu Val Lys Pro Gly Ala
1               5                   10                  15

Ser Val Lys Met Ser Cys Lys Ala Phe Gly Tyr Thr Phe Thr Ile Tyr
                20                  25                  30

Pro Ile Glu Trp Met Lys Gln Asn His Gly Lys Ser Leu Glu Trp Ile
            35                  40                  45

Gly Asn Phe His Pro Tyr Asn Gly Asp Thr Asn Tyr Asn Glu Lys Phe
        50                  55                  60

Lys Gly Lys Ala Lys Leu Thr Val Glu Lys Ser Ser Ser Thr Val Tyr
65                  70                  75                  80

Leu Glu Leu Ser Arg Leu Thr Ser Asp Asp Ser Ala Val Tyr Tyr Cys
                85                  90                  95

Ala Arg Gly Gly Thr Gly Ser Phe Asp Tyr Trp Gly Gln Gly Thr Ser
            100                 105                 110

Leu Thr Val Ser Ser
        115

<210> SEQ ID NO 99
<211> LENGTH: 108
<212> TYPE: PRT
<213> ORGANISM: Mus sp.

<400> SEQUENCE: 99

Glu Thr Thr Val Thr Gln Ser Pro Ala Ile Met Ala Ala Ser Leu Gly
1               5                   10                  15

Gln Lys Val Thr Met Thr Cys Ser Ala Ser Ser Ser Val Ser Ser Thr
                20                  25                  30

Tyr Leu His Trp Tyr Gln Gln Lys Ser Gly Ala Ser Pro Lys Pro Leu
            35                  40                  45

Ile Tyr Arg Thr Ser Thr Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Gln Gln Trp Ser Gly Tyr Pro
                85                  90                  95

Phe Thr Phe Gly Ser Gly Thr Arg Leu Glu Ile Lys
            100                 105

<210> SEQ ID NO 100
<211> LENGTH: 12
<212> TYPE: DNA
<213> ORGANISM: Artificial Sequence
<220> FEATURE:
<223> OTHER INFORMATION: Synthetic Construct

<400> SEQUENCE: 100
tgccaacaat gg                                                        12

<210> SEQ ID NO 101
<211> LENGTH: 108
<212> TYPE: PRT
<213> ORGANISM: Artificial Sequence
<220> FEATURE:
<223> OTHER INFORMATION: Synthetic Construct

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Ser Leu Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Synthetic Construct

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Ser Ile Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile
            100                 105

<210> SEQ ID NO 103
<211> LENGTH: 108
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Ser Trp Ser Ser Arg Val Ser Ser Thr
            20                  25                  30

Tyr Leu Phe Trp Tyr Gln Gln Lys Pro Gly Lys Ala Pro Lys Leu Leu

```
                35                  40                  45
Ile Tyr Arg Thr Ser Thr Leu Ala Ser Gly Val Pro Ser Arg Phe Ser
        50                  55                  60
Gly Ser Gly Ser Gly Thr Asp Phe Thr Leu Thr Ile Ser Ser Leu Gln
 65                 70                  75                  80
Pro Glu Asp Phe Ala Thr Tyr Tyr Cys Gln Gln Trp Ser Gly Tyr Pro
                85                  90                  95
Phe Thr Phe Gly Gly Gly Thr Lys Val Glu Ile Lys
            100                 105

<210> SEQ ID NO 104
<211> LENGTH: 108
<212> TYPE: PRT
<213> ORGANISM: Artificial Sequence
<220> FEATURE:
<223> OTHER INFORMATION: Synthetic Construct

<400> SEQUENCE: 104

Asp Ile Gln Met Thr Gln Ser Pro Ser Ser Leu Ser Ala Ser Val Gly
 1               5                  10                  15
Asp Arg Val Thr Ile Thr Cys Ser Ala Gly Ser Arg Val Ser Ser Thr
                20                  25                  30
Tyr Leu Phe Trp Tyr Gln Gln Lys Pro Gly Lys Ala Pro Lys Leu Leu
            35                  40                  45
Ile Tyr Arg Thr Ser Thr Leu Ala Ser Gly Val Pro Ser Arg Phe Ser
        50                  55                  60
Gly Ser Gly Ser Gly Thr Asp Phe Thr Leu Thr Ile Ser Ser Leu Gln
 65                 70                  75                  80
Pro Glu Asp Phe Ala Thr Tyr Tyr Cys Gln Gln Trp Ser Gly Tyr Pro
                85                  90                  95
Phe Thr Phe Gly Gly Gly Thr Lys Val Glu Ile Lys
            100                 105

<210> SEQ ID NO 105
<211> LENGTH: 108
<212> TYPE: PRT
<213> ORGANISM: Artificial Sequence
<220> FEATURE:
<223> OTHER INFORMATION: Synthetic Construct

<400> SEQUENCE: 105

Asp Ile Gln Met Thr Gln Ser Pro Ser Ser Leu Ser Ala Ser Val Gly
 1               5                  10                  15
Asp Arg Val Thr Ile Thr Cys Ser Ala Ser Ser Arg Val Val Ser Thr
                20                  25                  30
Tyr Leu Phe Trp Tyr Gln Gln Lys Pro Gly Lys Ala Pro Lys Leu Leu
            35                  40                  45
Ile Tyr Arg Thr Ser Thr Leu Ala Ser Gly Val Pro Ser Arg Phe Ser
        50                  55                  60
Gly Ser Gly Ser Gly Thr Asp Phe Thr Leu Thr Ile Ser Ser Leu Gln
 65                 70                  75                  80
Pro Glu Asp Phe Ala Thr Tyr Tyr Cys Gln Gln Trp Ser Gly Tyr Pro
                85                  90                  95
Phe Thr Phe Gly Gly Gly Thr Lys Val Glu Ile Lys
            100                 105

<210> SEQ ID NO 106
<211> LENGTH: 108
```

```
<212> TYPE: PRT
<213> ORGANISM: Artificial Sequence
<220> FEATURE:
<223> OTHER INFORMATION: Synthetic Construct

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys
            100                 105

<210> SEQ ID NO 107
<211> LENGTH: 108
<212> TYPE: PRT
<213> ORGANISM: Artificial Sequence
<220> FEATURE:
<223> OTHER INFORMATION: Synthetic Construct

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Ala Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys
            100                 105

<210> SEQ ID NO 108
<211> LENGTH: 108
<212> TYPE: PRT
<213> ORGANISM: Artificial Sequence
<220> FEATURE:
<223> OTHER INFORMATION: Synthetic Construct

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Trp Leu Ala Ser Gly Val Pro Ser Arg Phe Ser
```

```
            50                  55                  60
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                 85                  90                  95

Phe Thr Phe Gly Gly Gly Thr Lys Val Glu Ile Lys
            100                 105
```

<210> SEQ ID NO 109
<211> LENGTH: 108
<212> TYPE: PRT
<213> ORGANISM: Artificial Sequence
<220> FEATURE:
<223> OTHER INFORMATION: Synthetic Construct

<400> SEQUENCE: 109

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Arg Val Ser Ser Thr
                 20                  25                  30

Tyr Leu Phe Trp Tyr Gln Gln Lys Pro Gly Lys Ala Pro Lys Leu Leu
             35                  40                  45

Ile Tyr Arg Thr Ser Thr Gly Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                 85                  90                  95

Phe Thr Phe Gly Gly Gly Thr Lys Val Glu Ile Lys
            100                 105
```

<210> SEQ ID NO 110
<211> LENGTH: 108
<212> TYPE: PRT
<213> ORGANISM: Artificial Sequence
<220> FEATURE:
<223> OTHER INFORMATION: Synthetic Construct

<400> SEQUENCE: 110

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Arg Val Ser Ser Thr
                 20                  25                  30

Tyr Leu Phe Trp Tyr Gln Gln Lys Pro Gly Lys Ala Pro Lys Leu Leu
             35                  40                  45

Ile Tyr Arg Thr Ser Thr Leu Thr Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                 85                  90                  95

Phe Thr Phe Gly Gly Gly Thr Lys Val Glu Ile Lys
            100                 105
```

<210> SEQ ID NO 111
<211> LENGTH: 108
<212> TYPE: PRT
<213> ORGANISM: Artificial Sequence
<220> FEATURE:

<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Val Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys
            100                 105

<210> SEQ ID NO 112
<211> LENGTH: 108
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Leu Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys
            100                 105

<210> SEQ ID NO 113
<211> LENGTH: 108
<212> TYPE: PRT
<213> ORGANISM: Artificial Sequence
<220> FEATURE:
<223> OTHER INFORMATION: Synthetic Construct

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln

-continued

```
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 114
<211> LENGTH: 108
<212> TYPE: PRT
<213> ORGANISM: Artificial Sequence
<220> FEATURE:
<223> OTHER INFORMATION: Synthetic Construct

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 115
<211> LENGTH: 108
<212> TYPE: PRT
<213> ORGANISM: Artificial Sequence
<220> FEATURE:
<223> OTHER INFORMATION: Synthetic Construct

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Leu Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 116
<211> LENGTH: 108
<212> TYPE: PRT
<213> ORGANISM: Artificial Sequence
<220> FEATURE:
<223> OTHER INFORMATION: Synthetic Construct

<400> SEQUENCE: 116
```

US 8,765,129 B2
117                                                                                    118
-continued Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 117
<211> LENGTH: 108
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 118
<211> LENGTH: 108
<212> TYPE: PRT
<213> ORGANISM: Artificial Sequence
<220> FEATURE:
<223> OTHER INFORMATION: Synthetic Construct

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro

Phe Val Phe Gly Gly Gly Thr Lys Val Glu Ile Lys
            100                 105

<210> SEQ ID NO 119
<211> LENGTH: 108
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 120
<211> LENGTH: 108
<212> TYPE: PRT
<213> ORGANISM: Artificial Sequence
<220> FEATURE:
<223> OTHER INFORMATION: Synthetic Construct

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 121
<211> LENGTH: 108
<212> TYPE: PRT
<213> ORGANISM: Artificial Sequence
<220> FEATURE:
<223> OTHER INFORMATION: Synthetic Construct

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 122
<211> LENGTH: 108
<212> TYPE: PRT
<213> ORGANISM: Artificial Sequence
<220> FEATURE:
<223> OTHER INFORMATION: Synthetic Construct

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Thr Phe Gly Gly Gly Thr Lys Val Glu Ile Lys
            100                 105

<210> SEQ ID NO 123
<211> LENGTH: 108
<212> TYPE: PRT
<213> ORGANISM: Artificial Sequence
<220> FEATURE:
<223> OTHER INFORMATION: Synthetic Construct

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys

<210> SEQ ID NO 124
<211> LENGTH: 108
<212> TYPE: PRT
<213> ORGANISM: Artificial Sequence
<220> FEATURE:
<223> OTHER INFORMATION: Synthetic Construct

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Thr Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 125
<211> LENGTH: 108
<212> TYPE: PRT
<213> ORGANISM: Artificial Sequence
<220> FEATURE:
<223> OTHER INFORMATION: Synthetic Construct

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Ser Thr
            20                  25                  30

Tyr Leu Phe Trp Tyr Gln Gln Lys Pro Gly Lys Ala Pro Lys Leu Leu
        35                  40                  45

Ile Tyr Arg Thr Ser Pro Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Phe Val Phe Gly Gly Gly Thr Lys Val Glu Ile Lys
            100                 105

<210> SEQ ID NO 126
<211> LENGTH: 108
<212> TYPE: PRT
<213> ORGANISM: Artificial Sequence
<220> FEATURE:
<223> OTHER INFORMATION: Synthetic Construct

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Ser Ala Glu Ser Arg Val Ser Ser Thr
            20                  25                  30

Tyr Leu Phe Trp Tyr Gln Gln Lys Pro Gly Lys Ala Pro Lys Leu Leu
            35                  40                  45

Ile Tyr Arg Thr Ser Pro Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                 85                  90                  95

Phe Thr Phe Gly Gly Gly Thr Lys Val Glu Ile Lys
            100                 105

<210> SEQ ID NO 127
<211> LENGTH: 108
<212> TYPE: PRT
<213> ORGANISM: Artificial Sequence
<220> FEATURE:
<223> OTHER INFORMATION: Synthetic Construct

<400> SEQUENCE: 127

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Arg Val Ser Ser Thr
                 20                  25                  30

Tyr Leu Phe Trp Tyr Gln Gln Lys Pro Gly Lys Ala Pro Lys Leu Leu
            35                  40                  45

Ile Tyr Arg Thr Ser Thr Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                 85                  90                  95

Phe Thr Phe Gly Gly Gly Thr Lys Val Glu Ile Lys
            100                 105

<210> SEQ ID NO 128
<211> LENGTH: 117
<212> TYPE: PRT
<213> ORGANISM: Artificial Sequence
<220> FEATURE:
<223> OTHER INFORMATION: Synthetic Construct

<400> SEQUENCE: 128

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ile Tyr
                 20                  25                  30

Pro Ile Ser Trp Val Arg Gln Ala Pro Gly Gln Gly Leu Glu Trp Met
            35                  40                  45

Gly Asn Phe His Pro Tyr Leu Asp Thr Asn Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Thr Gly Ser Phe Asp Tyr Trp Gly Gln Gly Thr Thr
            100                 105                 110

Val Thr Val Ser Ser

<210> SEQ ID NO 129
<211> LENGTH: 117
<212> TYPE: PRT
<213> ORGANISM: Artificial Sequence
<220> FEATURE:
<223> OTHER INFORMATION: Synthetic Construct

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 130
<211> LENGTH: 117
<212> TYPE: PRT
<213> ORGANISM: Artificial Sequence
<220> FEATURE:
<223> OTHER INFORMATION: Synthetic construct

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Trp Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 131
<211> LENGTH: 117
<212> TYPE: PRT
<213> ORGANISM: Artificial Sequence
<220> FEATURE:
<223> OTHER INFORMATION: Synthetic Construct

<400> SEQUENCE: 131

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Thr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 132
<211> LENGTH: 117
<212> TYPE: PRT
<213> ORGANISM: Artificial Sequence
<220> FEATURE:
<223> OTHER INFORMATION: Synthetic Construct

<400> SEQUENCE: 132

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Leu Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 133
<211> LENGTH: 117
<212> TYPE: PRT
<213> ORGANISM: Artificial Sequence
<220> FEATURE:
<223> OTHER INFORMATION: Synthetic Construct

<400> SEQUENCE: 133

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Asn Glu Lys Phe
```

```
                        50                  55                  60
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Thr Gly Ser Phe Asp Tyr Trp Gly Gln Gly Thr Thr
                100                 105                 110

Val Thr Val Ser Ser
            115

<210> SEQ ID NO 134
<211> LENGTH: 117
<212> TYPE: PRT
<213> ORGANISM: Artificial Sequence
<220> FEATURE:
<223> OTHER INFORMATION: Synthetic Construct

<400> SEQUENCE: 134

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Ile Tyr
                 20                  25                  30

Pro Ile Ser Trp Val Arg Gln Ala Pro Gly Gln Gly Leu Glu Trp Met
             35                  40                  45

Gly Asn Phe His Pro Tyr Leu Gly Met Thr Asn Tyr Asn Glu Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Thr Gly Ser Phe Asp Tyr Trp Gly Gln Gly Thr Thr
                100                 105                 110

Val Thr Val Ser Ser
            115

<210> SEQ ID NO 135
<211> LENGTH: 117
<212> TYPE: PRT
<213> ORGANISM: Artificial Sequence
<220> FEATURE:
<223> OTHER INFORMATION: Synthetic Construct

<400> SEQUENCE: 135

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Ile Tyr
                 20                  25                  30

Pro Ile Ser Trp Val Arg Gln Ala Pro Gly Gln Gly Leu Glu Trp Met
             35                  40                  45

Gly Asn Phe His Pro Tyr Leu Gly Asp Ala Asn Tyr Asn Glu Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Thr Gly Ser Phe Asp Tyr Trp Gly Gln Gly Thr Thr
                100                 105                 110
```

```
Val Thr Val Ser Ser
        115
```

<210> SEQ ID NO 136
<211> LENGTH: 117
<212> TYPE: PRT
<213> ORGANISM: Artificial Sequence
<220> FEATURE:
<223> OTHER INFORMATION: Synthetic Construct

<400> SEQUENCE: 136

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Phe Gly Ser Phe Asp Tyr Trp Gly Gln Gly Thr Thr
            100                 105                 110

Val Thr Val Ser Ser
        115
```

<210> SEQ ID NO 137
<211> LENGTH: 117
<212> TYPE: PRT
<213> ORGANISM: Artificial Sequence
<220> FEATURE:
<223> OTHER INFORMATION: Synthetic Construct

<400> SEQUENCE: 137

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ala Phe Asp Tyr Trp Gly Gln Gly Thr Thr
            100                 105                 110

Val Thr Val Ser Ser
        115
```

<210> SEQ ID NO 138
<211> LENGTH: 117
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Asp Thr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Pro Tyr Trp Gly Gln Gly Thr Thr
            100                 105                 110

Val Thr Val Ser Ser
        115

<210> SEQ ID NO 139
<211> LENGTH: 117
<212> TYPE: PRT
<213> ORGANISM: Artificial Sequence
<220> FEATURE:
<223> OTHER INFORMATION: Synthetic Construct

<400> SEQUENCE: 139

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Glu Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Leu Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 140
<211> LENGTH: 117
<212> TYPE: PRT
<213> ORGANISM: Artificial Sequence
<220> FEATURE:
<223> OTHER INFORMATION: Synthetic Construct

<400> SEQUENCE: 140

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

```
Gly Asn Phe His Pro Tyr Leu Gly Asp Thr Lys Tyr Val Glu Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Thr Gly Ser Phe Asp Tyr Trp Gly Gln Gly Thr Thr
                100                 105                 110

Val Thr Val Ser Ser
        115
```

<210> SEQ ID NO 141
<211> LENGTH: 117
<212> TYPE: PRT
<213> ORGANISM: Artificial Sequence
<220> FEATURE:
<223> OTHER INFORMATION: Synthetic Construct

<400> SEQUENCE: 141

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ile Tyr
                 20                  25                  30

Pro Ile Ser Trp Val Arg Gln Ala Pro Gly Gln Gly Leu Glu Trp Met
             35                  40                  45

Gly Asn Phe His Pro Tyr Leu Gly Asp Thr Arg Tyr Val Glu Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Thr Gly Ser Phe Asp Tyr Trp Gly Gln Gly Thr Thr
                100                 105                 110

Val Thr Val Ser Ser
        115
```

<210> SEQ ID NO 142
<211> LENGTH: 117
<212> TYPE: PRT
<213> ORGANISM: Artificial Sequence
<220> FEATURE:
<223> OTHER INFORMATION: Synthetic Construct

<400> SEQUENCE: 142

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Leu Ile Tyr
                 20                  25                  30

Pro Ile Ser Trp Val Arg Gln Ala Pro Gly Gln Gly Leu Glu Trp Met
             35                  40                  45

Gly Asn Phe His Pro Tyr Leu Gly Val Thr Lys Tyr Leu Glu Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Thr Gly Ser Phe Asp Tyr Trp Gly Gln Gly Thr Thr
                100                 105                 110
```

Val Thr Val Ser Ser
        115

<210> SEQ ID NO 143
<211> LENGTH: 117
<212> TYPE: PRT
<213> ORGANISM: Artificial Sequence
<220> FEATURE:
<223> OTHER INFORMATION: Synthetic Construct

<400> SEQUENCE: 143

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Lys Tyr Val Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 144
<211> LENGTH: 117
<212> TYPE: PRT
<213> ORGANISM: Artificial Sequence
<220> FEATURE:
<223> OTHER INFORMATION: Synthetic Construct

<400> SEQUENCE: 144

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Lys Tyr Leu Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 145
<211> LENGTH: 117
<212> TYPE: PRT
<213> ORGANISM: Artificial Sequence
<220> FEATURE:
<223> OTHER INFORMATION: Synthetic Construct

<400> SEQUENCE: 145

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Leu Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 146
<211> LENGTH: 117
<212> TYPE: PRT
<213> ORGANISM: Artificial Sequence
<220> FEATURE:
<223> OTHER INFORMATION: Synthetic Construct

<400> SEQUENCE: 146

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Leu Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 147
<211> LENGTH: 117
<212> TYPE: PRT
<213> ORGANISM: Artificial Sequence
<220> FEATURE:
<223> OTHER INFORMATION: Synthetic Construct

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Val Glu Lys Phe
            50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
                100                 105                 110

Val Thr Val Ser Ser
        115

<210> SEQ ID NO 148
<211> LENGTH: 117
<212> TYPE: PRT
<213> ORGANISM: Artificial Sequence
<220> FEATURE:
<223> OTHER INFORMATION: Synthetic Construct

<400> SEQUENCE: 148

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
                20                  25                  30

Pro Ile Ser Trp Val Arg Gln Ala Pro Gly Gln Gly Leu Glu Trp Met
            35                  40                  45

Gly Asn Phe His Pro Tyr Leu Gly Val Thr Asn Tyr Leu Glu Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
                100                 105                 110

Val Thr Val Ser Ser
        115

<210> SEQ ID NO 149
<211> LENGTH: 117
<212> TYPE: PRT
<213> ORGANISM: Artificial Sequence
<220> FEATURE:
<223> OTHER INFORMATION: Synthetic Construct

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
                20                  25                  30

Pro Ile Ser Trp Val Arg Gln Ala Pro Gly Gln Gly Leu Glu Trp Met
            35                  40                  45

Gly Asn Phe His Pro Tyr Leu Gly Asp Thr Asn Tyr Leu Glu Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr

Val Thr Val Ser Ser
        115

<210> SEQ ID NO 150
<211> LENGTH: 117
<212> TYPE: PRT
<213> ORGANISM: Artificial Sequence
<220> FEATURE:
<223> OTHER INFORMATION: Synthetic Construct

<400> SEQUENCE: 150

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Leu Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 151
<211> LENGTH: 117
<212> TYPE: PRT
<213> ORGANISM: Artificial Sequence
<220> FEATURE:
<223> OTHER INFORMATION: Synthetic Construct

<400> SEQUENCE: 151

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Leu Ile Tyr
            20                  25                  30

Pro Ile Ser Trp Val Arg Gln Ala Pro Gly Gln Gly Leu Glu Trp Met
        35                  40                  45

Gly Asn Phe His Pro Tyr Leu Gly Val Thr Asn Tyr Val Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Ser Phe Asp Tyr Trp Gly Gln Gly Thr Thr
            100                 105                 110

Val Thr Val Ser Ser
        115

<210> SEQ ID NO 152
<211> LENGTH: 117
<212> TYPE: PRT
<213> ORGANISM: Artificial Sequence
<220> FEATURE:

<223> OTHER INFORMATION: Synthetic Construct

<400> SEQUENCE: 152

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Leu Ile Tyr
            20                  25                  30
Pro Ile Ser Trp Val Arg Gln Ala Pro Gly Gln Gly Leu Glu Trp Met
        35                  40                  45
Gly Asn Phe His Pro Tyr Leu Gly Val Thr Asn Tyr Leu Glu Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Thr Gly Ser Phe Asp Tyr Trp Gly Gln Gly Thr Thr
            100                 105                 110
Val Thr Val Ser Ser
        115

<210> SEQ ID NO 153
<211> LENGTH: 645
<212> TYPE: DNA
<213> ORGANISM: Artificial Sequence
<220> FEATURE:
<223> OTHER INFORMATION: Synthetic Construct

<400> SEQUENCE: 153

```
gacatccaga tgacccagtc tccatcctcc ctgtctgcat ctgtaggaga cagagtcacc    60
atcacttgca gtgccagctc acgcgtaagt tccacttact tgttctggta tcagcagaaa   120
ccagggaaag cccctaagct cctgatctat aggacatcca ccctgacctc tggagtccca   180
tcaaggttca gtggcagtgg atctgggaca gatttcactc tcaccatcag cagtctgcaa   240
cctgaagatt ttgcaactta ctattgtcag cagtggagtg gttacccatt cgtgttcggc   300
ggagggacca aggtggagat caaacggact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgc                   645
```

<210> SEQ ID NO 154
<211> LENGTH: 23
<212> TYPE: PRT
<213> ORGANISM: Homo sapiens

<400> SEQUENCE: 154

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 155
<211> LENGTH: 645
<212> TYPE: DNA
<213> ORGANISM: Artificial Sequence

```
<220> FEATURE:
<223> OTHER INFORMATION: Synthetic Construct

<400> SEQUENCE: 155
gacatccaga tgacccagtc tccatcctcc ctgtctgcat ctgtaggaga cagagtcacc      60
atcacttgca gtgccagctc acgcgtaagt tccacttact tgttctggta tcagcagaaa    120
ccagggaaag cccctaagct cctgatctat aggacatccc cctggcctc tggagtccca    180
tcaaggttca gtggcagtgg atctgggaca gatttcactc tcaccatcag cagtctgcaa    240
cctgaagatt ttgcaactta ctattgtcag cagtggagtg gttacccatt cgtgttcggc    300
ggagggacca aggtggagat caaacggact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgc                    645

<210> SEQ ID NO 156
<211> LENGTH: 32
<212> TYPE: PRT
<213> ORGANISM: Homo sapiens

<400> SEQUENCE: 156

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 157
<211> LENGTH: 25
<212> TYPE: PRT
<213> ORGANISM: Homo sapiens

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 158
<211> LENGTH: 32
<212> TYPE: PRT
<213> ORGANISM: Homo sapiens

<400> SEQUENCE: 158

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 159
<211> LENGTH: 23
<212> TYPE: PRT
<213> ORGANISM: Homo sapiens

<400> SEQUENCE: 159

Asp Ile Gln Met Thr Gln Ser Pro Ser Thr Leu Ser Ala Ser Val Gly
1               5                   10                  15
```

```
Asp Arg Val Thr Ile Thr Cys
            20

<210> SEQ ID NO 160
<211> LENGTH: 32
<212> TYPE: PRT
<213> ORGANISM: Homo sapiens

<400> SEQUENCE: 160

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 161
<211> LENGTH: 32
<212> TYPE: PRT
<213> ORGANISM: Homo sapiens

<400> SEQUENCE: 161

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 162
<211> LENGTH: 6
<212> TYPE: DNA
<213> ORGANISM: Artificial Sequence
<220> FEATURE:
<223> OTHER INFORMATION: Synthetic Construct

<400> SEQUENCE: 162 ctcatc                                                         6
```